(12) United States Patent
Aoki

(10) Patent No.: US 11,045,145 B2
(45) Date of Patent: Jun. 29, 2021

(54) BUCKLE AND ON-VEHICLE SYSTEM

(71) Applicant: Hiroshi Aoki, Shiga (JP)

(72) Inventor: Hiroshi Aoki, Shiga (JP)

(73) Assignee: Joyson Safety Systems Japan K.K., Tokyo (JP)

(*) Notice: Subject to any disclaimer, the term of this patent is extended or adjusted under 35 U.S.C. 154(b) by 746 days.

(21) Appl. No.: 15/477,447

(22) Filed: Apr. 3, 2017

(65) Prior Publication Data

US 2017/0296128 A1    Oct. 19, 2017

(30) Foreign Application Priority Data

Apr. 14, 2016  (JP) .............................. JP2016-081279

(51) Int. Cl.
| | | |
|---|---|---|
| *A61B 5/00* | (2006.01) | |
| *A61B 5/113* | (2006.01) | |
| *A61B 5/024* | (2006.01) | |
| *A61B 5/08* | (2006.01) | |
| *A61B 5/18* | (2006.01) | |

(52) U.S. Cl.
CPC ............ *A61B 5/7207* (2013.01); *A61B 5/024* (2013.01); *A61B 5/08* (2013.01); *A61B 5/1135* (2013.01); *A61B 5/18* (2013.01); *A61B 5/6893* (2013.01); *A61B 2503/22* (2013.01)

(58) Field of Classification Search
CPC ................................ A61B 5/7207; A61B 5/08
See application file for complete search history.

(56) References Cited

U.S. PATENT DOCUMENTS 5,743,857 A * 4/1998 Shinoda .............. A61B 5/02116
                                                    600/492
2006/0224074 A1   10/2006 Ouchi et al.
2010/0049066 A1    2/2010 Hatakeyama
(Continued)

FOREIGN PATENT DOCUMENTS

JP    2004-290324    10/2004
JP    2006-149882     6/2006
(Continued)

OTHER PUBLICATIONS

English Translation of JP2013216187 (Year: 2013).*
(Continued)

*Primary Examiner* — Daniel L Cerioni
*Assistant Examiner* — Yasmeen S Warsi
(74) *Attorney, Agent, or Firm* — IPUSA, PLLC

(57) ABSTRACT

A buckle includes a main body connectable to a tongue attached to a seatbelt of a vehicle, a sensor disposed in the main body or in a support member that supports the main body, the sensor configured to produce a sensor output signal whose waveform changes in response to movement of an object situated in a seat of the vehicle, a detection unit configured to detect, from the sensor output signal produced by the sensor, vital-sign signal components indicative of a vital sign that is at least either respiration or pulse beat, a generation unit configured to evaluate reliability of the vital-sign signal components detected by the detection unit and to generate vital-sign information about the vital sign from a reliable one of the vital-sign signal components, and an output unit configured to output the vital-sign information generated by the generation unit.

14 Claims, 15 Drawing Sheets

(56) References Cited

U.S. PATENT DOCUMENTS

| | | | |
|---|---|---|---|
| 2010/0222687 A1* | 9/2010 | Thijs | A61B 8/488 |
| | | | 600/508 |
| 2013/0033382 A1* | 2/2013 | Fung | A61B 5/6893 |
| | | | 340/573.1 |
| 2015/0133804 A1 | 5/2015 | Sugiyama et al. | |

FOREIGN PATENT DOCUMENTS

| | | |
|---|---|---|
| JP | 2006-271731 | 10/2006 |
| JP | 2010-120493 | 6/2010 |
| JP | 4697185 | 6/2011 |
| JP | 2012-105835 | 6/2012 |
| JP | 2012-130391 | 7/2012 |
| JP | 2013-220322 | 10/2013 |
| JP | 2014-036800 | 2/2014 |
| JP | 5494432 | 5/2014 |
| JP | 2014-226451 | 12/2014 |
| JP | 2015-123160 | 7/2015 |
| JP | 5952063 | 7/2016 |

OTHER PUBLICATIONS

English Translation of JP2013220322 (Year: 2013).*

Martz, Harry F., and Paul H. Kvam. "Detecting trends and patterns in reliability data over time using exponentially weighted moving-averages." Reliability Engineering & System Safety 51.2 (1996): 201-207. (Year: 1996).*

Japanese Office Action dated Jul. 28, 2020 (JP Patent Application No. 2016-081279).

* cited by examiner

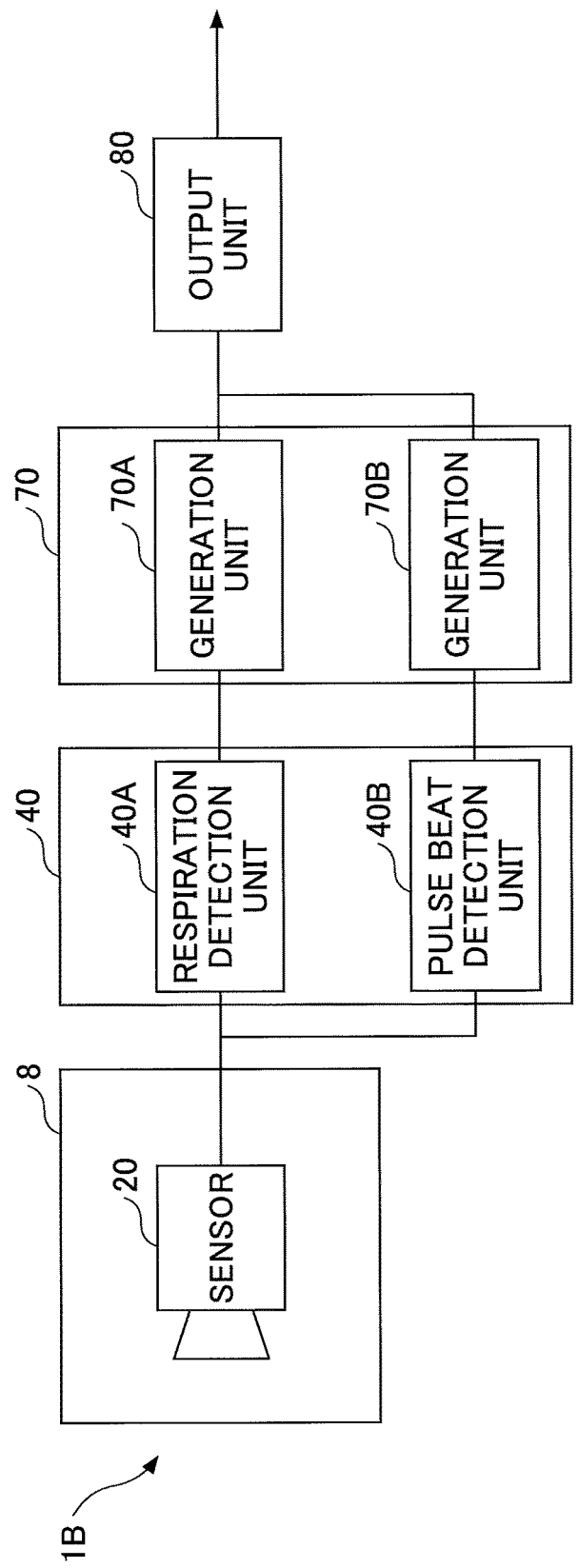

BUCKLE AND ON-VEHICLE SYSTEM

BACKGROUND OF THE INVENTION

1. Field of the Invention

The disclosures herein generally relate to a buckle and an on-vehicle system.

2. Description of the Related Art

A buckle having a sensor for detecting the respiratory condition of a vehicle seat occupant by means of infrared light is known in the art (see Patent Document 1, for example).

The movement of an occupant body or vibration due to the movement of a traveling vehicle causes the accuracy of detection of respiration or pulse beat to be lowered. In such a case, the related-art technology has difficulty in acquiring accurate information regarding respiration or pulse beat.

There may be a need to provide a buckle and an on-vehicle system that collect information regarding respiration or pulse beat with increased accuracy.

RELATED-ART DOCUMENTS

Patent Document

[Patent Document 1] Japanese Patent Application Publication No. 2013-216187

SUMMARY OF THE INVENTION

It is a general object of the present invention to provide a buckle and an on-vehicle system that substantially obviate one or more problems caused by the limitations and disadvantages of the related art.

According to an embodiment, a buckle includes a main body connectable to a tongue attached to a seatbelt of a vehicle, a sensor disposed in the main body or in a support member that supports the main body, the sensor configured to produce a sensor output signal whose waveform changes in response to movement of an object situated in a seat of the vehicle, a detection unit configured to detect, from the sensor output signal produced by the sensor, vital-sign signal components indicative of a vital sign that is at least either respiration or pulse beat, a generation unit configured to evaluate reliability of the vital-sign signal components detected by the detection unit and to generate vital-sign information about the vital sign from a reliable one of the vital-sign signal components, and an output unit configured to output the vital-sign information generated by the generation unit.

According to an embodiment, an on-vehicle system includes a buckle connectable to a tongue attached to a seatbelt of a vehicle, a sensor disposed in the buckle or in a support member that supports the buckle, the sensor configured to produce a sensor output signal whose waveform changes in response to movement of an object situated in a seat of the vehicle, a detection unit configured to detect, from the sensor output signal produced by the sensor, vital-sign signal components indicative of a vital sign that is at least either respiration or pulse beat, a generation unit configured to evaluate reliability of the vital-sign signal components detected by the detection unit and to generate vital-sign information about the vital sign from a reliable one of the vital-sign signal components, and an output unit configured to output the vital-sign information generated by the generation unit.

According to at least one embodiment, the detection unit detects, from the sensor output signal produced by the sensor, vital-sign signal components indicative of a vital sign that is at least either respiration or pulse beat. The generation unit then evaluates the reliability of the vital-sign signal components detected by the detection unit, and generates vital-sign information about the vital sign from a reliable one of the vital-sign signal components, thereby improving the reliability of generated vital-sign information. The output unit outputs the vital-sign information generated by the generation unit, thereby providing the vital-sign information with improved reliability.

According to at least one embodiment, information (i.e., vital-sign information) about respiration and pulse beat is collected with increased accuracy.

BRIEF DESCRIPTION OF THE DRAWINGS

Other objects and further features of the present invention will be apparent from the following detailed description when read in conjunction with the accompanying drawings, in which:

FIG. 20 is a block diagram illustrating another example of the configuration of an on-vehicle system.

DESCRIPTION OF THE PREFERRED EMBODIMENTS

In the following, embodiments will be described with reference to the accompanying drawings.

Figure 1:
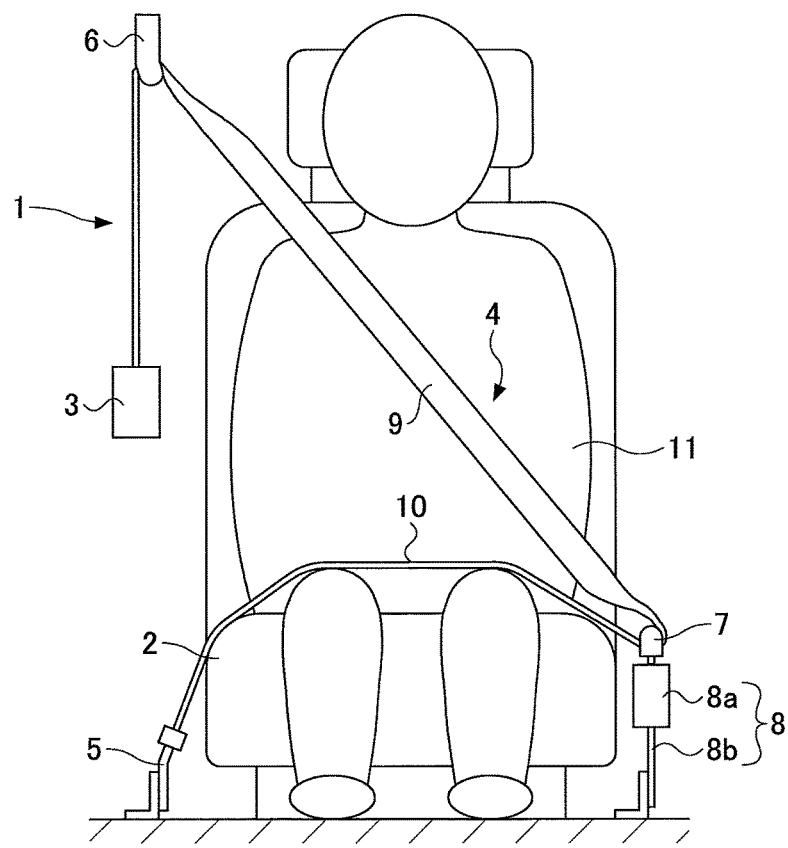
FIG. 1 is a drawing illustrating an example of the configuration of an on-vehicle system.

FIG. 1 is a drawing illustrating an example of the configuration of a seatbelt apparatus 1 according to an embodiment. The seatbelt apparatus 1 is an example of an on-vehicle system installed in a vehicle. The seatbelt apparatus 1 includes a seatbelt 4, a retractor 3, a shoulder anchor 6, a tongue 7, and a buckle 8.

The seatbelt 4, which is an example of webbing for restraining an occupant 11 sitting in a vehicle seat 2, is implemented as a band-shaped member reeled in the retractor 3 in an extractable manner. A belt anchor 5 at the tip of the seatbelt 4 is fixed to the vehicle floor or to the seat 2.

The retractor 3 is an example of a reel apparatus that allows the seatbelt 4 to be retracted or extracted. Upon deceleration greater than a predetermined value being applied to the vehicle at the time of vehicle collision or the like, the retractor 3 restrains the seatbelt 4 from being extracted. The retractor 3 is fastened to the seat 2 or to the vehicle body in the proximity of the seat 2.

The shoulder anchor 6, which is an example of a loop member allowing the seatbelt 4 to pass therethrough, serves to guide the seatbelt 4 extracted from the retractor 3 toward the shoulder of the occupant.

The tongue 7, which is an example of a loop member allowing the seatbelt 4 to pass therethrough, is slidably attached to the seatbelt 4 that is guided by the shoulder anchor 6.

The buckle 8, which is a component detachably connectable to the tongue 7, may be secured to the vehicle floor or to the seat 2.

The buckle 8 includes a main body 8a and a stay 8b. The main body 8a is detachably connectable to the tongue 7. The stay 8b is an example of a support member that supports the main body 8a of the buckle 8. The stay 8b is fastened to the vehicle floor or to the seat 2.

With the tongue 7 being engaged with the buckle 8, the portion of the seatbelt 4 situated between the shoulder anchor 6 and the tongue 7 serves as a shoulder belt part 9 which restrains the chest and shoulder of the occupant. With the tongue 7 being engaged with the buckle 8, the portion of the seatbelt 4 situated between the belt anchor 5 and the tongue 7 serves as a lap belt part 10 which restrains the hips of the occupant.

Figure 2:
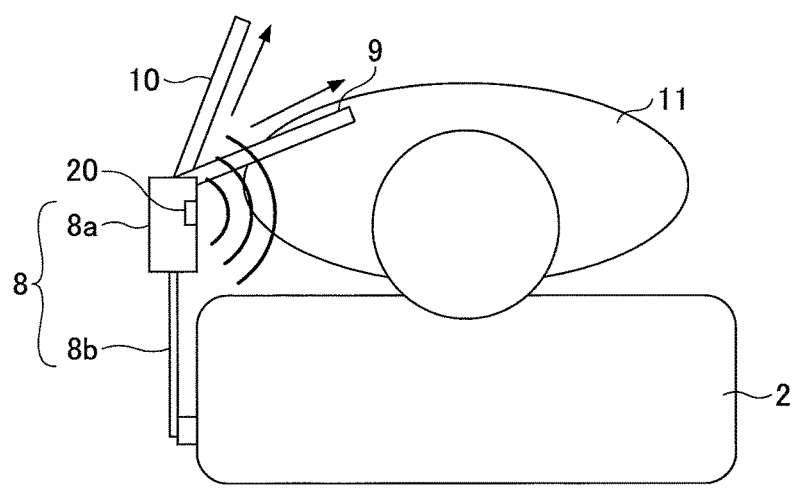
FIG. 2 is a drawing illustrating an occupant sitting in a seat as viewed from above.

FIG. 2 is a drawing illustrating the occupant 11 sitting in the seat 2 as viewed from above. FIG. 2 illustrates a backrest of the seat 2.

Respiration of the occupant 11 sitting in the seat 2 causes the body surface of the occupant 11 (e.g., the surface of the hips, the surface of the abdomen, the surface of the chest, and the like) to exhibit a minute displacement. Inhaling by the occupant 11 causes the body surface of the occupant 11 to expand in the vehicle front-rear direction as well as in the vehicle width direction. Exhaling by the occupant 11 causes the body surface of the occupant 11 to contract in the vehicle front-rear direction as well as in the vehicle width direction. Detecting the displacement of a body surface of the occupant 11 thus enables the detection of respiration of the occupant 11.

The buckle 8 serving as a means to detect the displacement of a body surface of the occupant 11 has a sensor 20 disposed on the main body 8a. The sensor 20 may alternatively be disposed on the stay 8b. The buckle 8 is situated at a lower position on one side of the occupant 11 sitting in the seat 2. The sensor 20 is disposed on the lateral face of the buckle 8 facing toward the occupant 11.

The sensor 20 is an example of an object detecting unit configured to detect the movement of an object on the vehicle seat 2 in a noncontact manner. The object on the seat 2 is not limited to the occupant 11, and may be a thing other than a human body such as the occupant 11. The sensor 20 produces a sensor output signal whose waveform changes in response to the movement of the object on the seat 2. The movement of the object is not limited to the movement of the object surface, but may as well be movement occurring inside the object.

The sensor 20 transmits and receives radio waves to detect the movement of the object on the vehicle seat 2 in a noncontact manner, for example. The sensor 20 transmits radio waves toward an upper space over the upper face of the vehicle seat 2, and receives the reflective waves of the transmitted radio waves to detect the movement of the object on the upper seat face.

Examples of radio waves transmitted and received by the sensor 20 may include radio waves in the VHF (i.e., very high frequency) band and microwaves in the UHF (i.e., ultrahigh frequency) band or the SHF (i.e., super high frequency) band. The VHF band is a frequency band from 30 MHz to 0.3 GHz. The UHF band is a frequency band from 0.3 GHz to 3 GHz. The SHF band is a frequency band from 3 GHz to 30 GHz.

Alternatively, the sensor 20 may be an object detecting unit configured to detect the movement of the object on the vehicle seat 2 in a noncontact manner in response to a change in electrostatic capacitance between the sensor electrode of the sensor 20 and the object.

Figure 3:
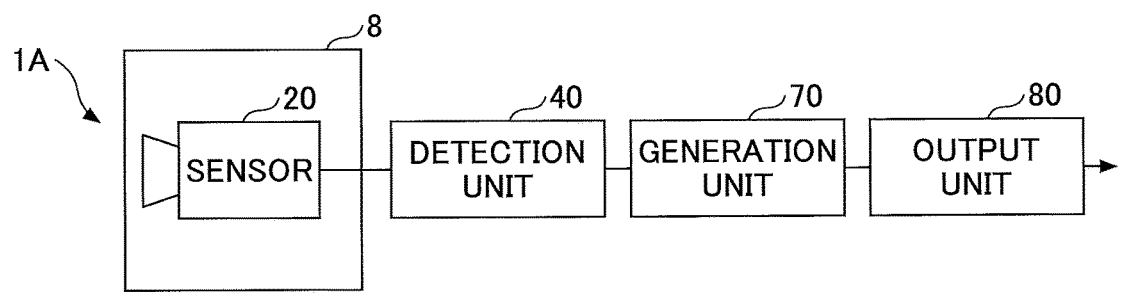
FIG. 3 is a block diagram illustrating an example of the configuration of an on-vehicle system.

FIG. 3 is a block diagram illustrating the configuration of a seatbelt apparatus 1A serving as an example of the seatbelt apparatus 1. The seatbelt apparatus 1A includes the buckle 8 having the sensor 20 attached thereto, a detection unit 40, a generation unit 70, and an output unit 80. The detection unit 40, the generation unit 70, and the output unit 80 are situated outside the buckle 8. The detection unit 40, the generation unit 70, and the output unit 80 may be implemented as one or more electronic control apparatuses (which may be referred to as an ECU) separate from the buckle 8, for example.

Part or all of the detection unit 40, the generation unit 70, and the output unit 80 may alternatively be situated in the buckle 8. Part or all of the detection unit 40 (see FIG. 13, which will be described later) may be situated in the buckle 8. The generation unit 70 and the output unit 80 may be situated in the ECU installed in the vehicle for the purpose of allowing easy access to vehicle information such as vehicle behavior data indicative of the behavior of the vehicle, which causes the shift of the object on the vehicle seat 2. The vehicle behavior data includes vehicle speed data, acceleration/deceleration data, yaw-rate data, steering angle data, and so on. The detection unit 40, the generation unit 70, and the output unit 80 may be implemented as a microcomputer having a central processing unit, for example.

Figure 4:
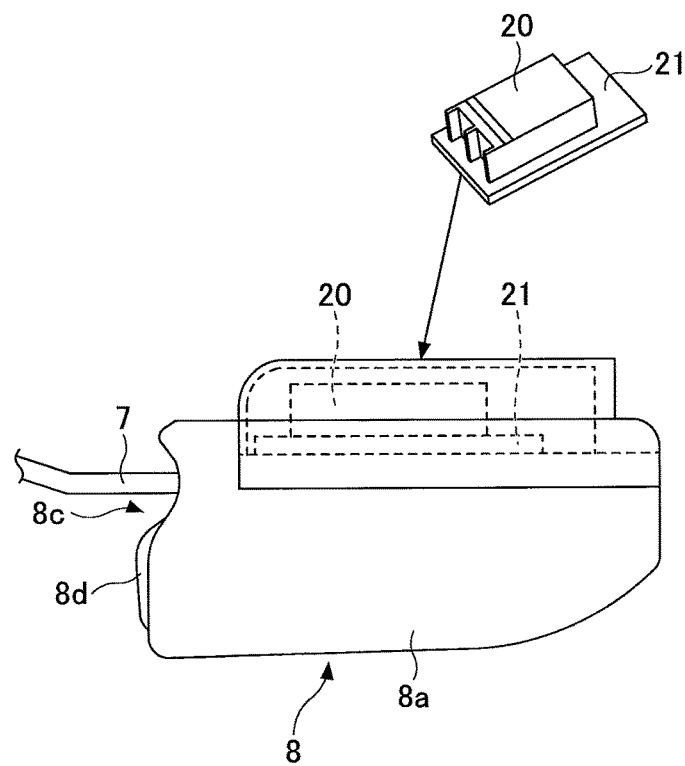
FIG. 4 is a side elevation view illustrating an example of the main body of a buckle.
Figure 5:
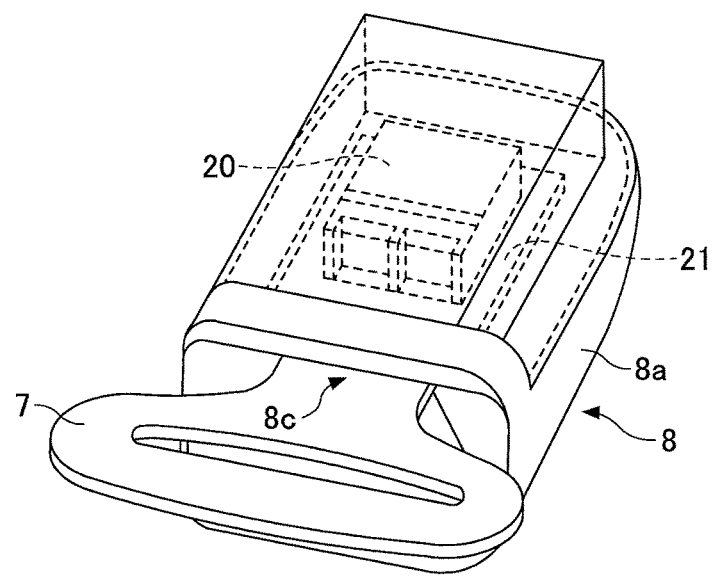
FIG. 5 is an axonometric view illustrating an example of the main body of a buckle.
Figure 6:
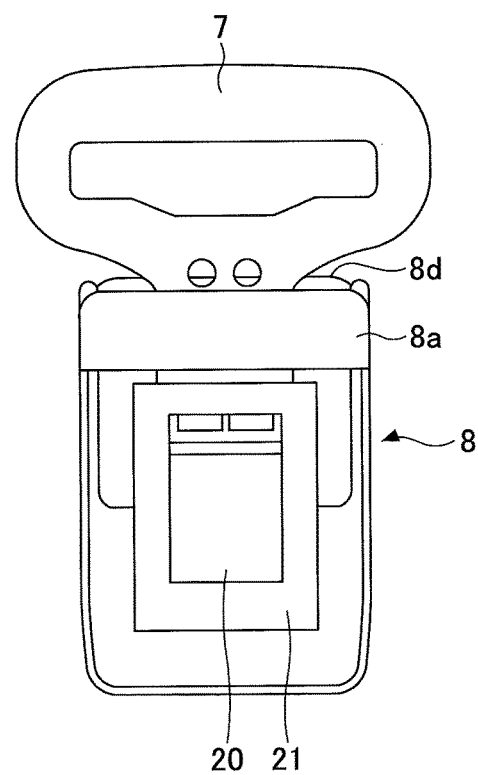
FIG. 6 is a plan view illustrating an example of the main body of a buckle.

FIG. 4 is a side elevation view illustrating an example of the main body 8a of the buckle 8. FIG. 5 is an axonometric view illustrating an example of the main body 8a of the buckle 8. FIG. 6 is a plan view illustrating an example of the main body 8a of the buckle 8a as viewed from the occupant side. The main body 8a includes an insertion opening 8c into which the metal plate of the tongue 7 is inserted, and further includes a button 8d used by the occupant to release the tongue 7.

The sensor 20 is embedded into the lateral face of the buckle 8 facing toward the seat 2 (i.e., toward the occupant sitting in the seat 2). In the case of the sensor 20 being configured to transmit and receive radio waves, the sensor 20 is preferably disposed between a shield plate 21 and the side face of the buckle 8 facing toward the seat 2 in order to prevent radio waves from travelling in useless directions. The shield plate 21 is embedded into the main body 8a to shield radio waves emitted from the sensor 20.

Figure 7:
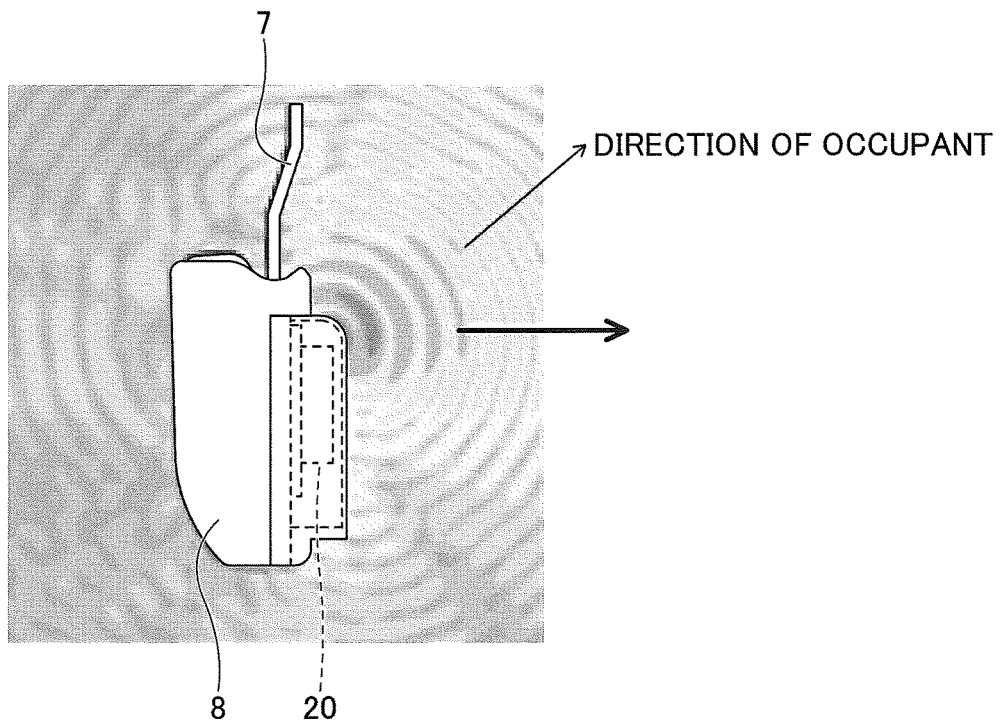
FIG. 7 is a view illustrating an example of radio wave radiation as seen in the side view of the buckle.
Figure 8:
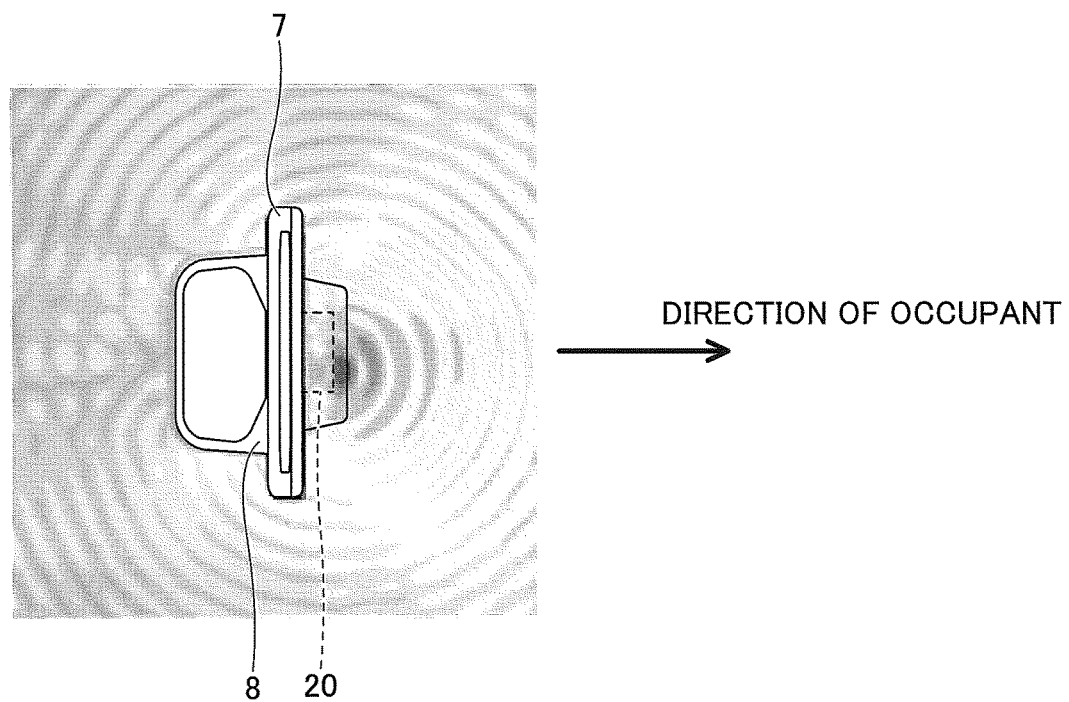
FIG. 8 is a view illustrating an example of radio wave radiation as seen in the top view of the buckle.

FIG. 7 is a view illustrating an example of radio wave radiation as seen in the side view of the buckle 8. FIG. 8 is a view illustrating an example of radio wave radiation as seen in the top view of the buckle 8.

The directions of radio wave radiation differ depending on the antenna for transmitting and receiving radio waves as well as the frequency of radio waves. The antenna may be installed on the sensor 20 at an angle directed toward the occupant, or may have the directivity oriented toward the direction of the occupant.

Radio waves transmitted from the transmission antenna of the sensor 20 disposed in the buckle 8 are reflected by the object on the seat. These reflected waves are received by the reception antenna of the sensor 20. The sensor 20 measures at least one of a change in the standing wave ratio, a change in the magnitude of the reflected waves, a change in the propagation delay time of the reflected waves relative to the transmitted waves, a change in the phase difference between the transmitted waves and the reflected waves, a change in the frequency difference between the transmitted waves and the reflected waves. Measuring at least one of these changes, the sensor 20 detects a relative positional change between the sensor 20 and the object on the seat 2 (i.e., sensor target).

These changes such as the change in the standing wave ratio are affected by the distance between the sensor 20 and the sensor target, the size of the sensor target, the shape of the reflective surface of the sensor target, and the physical property (e.g., metal surface, human body surface) of the sensor target.

In the case of transmitting and receiving radio waves of 100 MHz to 5 GHz, for example, the sensor 20 measures a change in the standing wave ratio to detect a relative positional change of the sensor target based on the obtained measurements. In the case of transmitting and receiving radio waves of 10 GHz to 100 GHz, for example, the sensor 20 measures changes in the propagation delay time and the Doppler frequency to detect a relative positional change of the sensor target based on the obtained measurements.

In the case of the sensor 20 being an electrostatic sensor driving the sensor electrodes with a frequency of 30 kHz to 1 MHz, for example, the sensor 20 measures a change in the electrostatic capacitance between the sensor target and the sensor electrodes to detect a relative positional change of the sensor target based on the measurements.

In this embodiment, as illustrated in FIG. 7 and FIG. 8, radio waves are transmitted toward an upper space over the seat 2 with a spread angle that is greater than or equal to 40 degrees and smaller than or equal to 90 degrees. Sharpening the directivity of radio waves enables the detection of a relative positional change in a narrow range. Conversely, broadening the directivity of radio waves enables the detection of a relative positional change in a broad range.

In the case of the sensor target being situated in the vicinity of the sensor 20, the accuracy of detection of a relative positional change is predominantly dependent on by the surrounding conditions near the sensor 20. Because of this, the sensor 20 can detect a relative positional change of the sensor target with high accuracy even when a plurality of other sensors in addition to the sensor 20 are present in the vehicle interior space or when the directivity of radio waves is off the desired angle to some extent.

As illustrated in FIG. 1 and FIG. 2, the side face of the buckle 8 faces the hip of the occupant 11 sitting in the seat 2, for example. The radio waves transmitted with a predetermined spread angle from the sensor 20 are reflected at the seat 2 and the abdomen (including the flank), resulting in the reflected waves arriving at the sensor 20. The sensor 20 thus detects a relative positional change between the buckle 8 and the abdomen (including the flank) in addition to a relative positional change between the buckle 8 and the hip.

Inhaling by the occupant 11 causes the flank to expand and come closer to the sensor 20, and also causes the anterior abdomen to bulge toward the front of the vehicle to bring about an increase in the area size of a radio wave reflective surface. As a result, the intensity of reflected waves increases. Especially when the occupant 11 inhales while wearing the seatbelt 4, the expansion of the chest of the occupant 11 serves to increase a tension of the seatbelt 4, which causes the buckle 8 to come closer to the seatbelt apparatus 1. This further serves to increase the intensity of reflected waves.

Exhaling by the occupant 11 causes the flank to contract and move away from the sensor 20, and also causes the anterior abdomen to move toward the rear of the vehicle to bring about a decrease in the area size of the radio wave reflective surface. As a result, the intensity of reflected waves decreases. Especially when the occupant 11 exhales while wearing the seatbelt 4, the contraction of the chest of the occupant 11 serves to decrease a tension of the seatbelt 4, which causes the buckle 8 to move away from the occupant 11. This further serves to decrease the intensity of reflected waves.

In this manner, the respiration of the occupant 11 is detectable as changes in the intensity of reflected waves. Detecting changes in the intensity of reflected waves and analyzing the frequency of signals synchronized with respiration enables the detection of respiration of the occupant 11. In the case of the frequency of radio waves falling within a frequency range responsive to blood flow, the pulse beat of the occupant 11 can be detected.

Respiration is detectable even when the seatbelt 4 is not used. When the seatbelt 4 is used, in particular, the seatbelt 4 is displaced in response to the positional changes of the body surface of the occupant 11. Such a displacement of the seatbelt 4 causes the buckle 8 to be displaced through the tongue 7. With this arrangement, more reliable detection of respiration and pulse beat than in the related art is possible.

Figure 9:
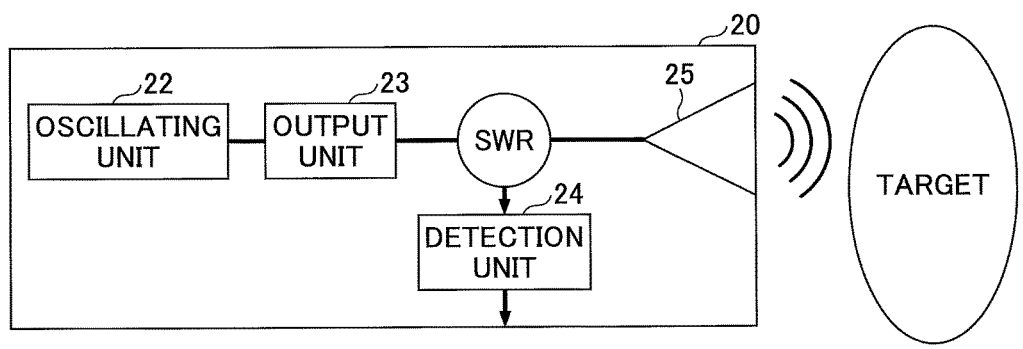
FIG. 9 is a drawing illustrating an example of the configuration of a sensor.

FIG. 9 is a drawing illustrating an example of the configuration of the sensor 20. The sensor 20 includes an oscillating unit 22, an output unit 23, a detection unit 24, and an antenna 25.

The oscillating unit 22 generates a signal oscillating at specific stable frequency. The output unit 23 feeds power to the antenna 25 based on the signal generated by the oscillating unit 22. Satisfactory matching provided at the antenna 25 enables the transmission of radio waves from the antenna 25 to space with suppressed reflection loss at the antenna 25. The standing wave ratio (i.e., SWR) refers to a ratio of the magnitude of a reflected wave to the magnitude of a traveling wave propagating from the output unit 23 to the antenna 25. With a stable output, a change in the reflected waves from the sensor target appears as a change in the SWR. The SWR exhibits cyclic changes as the buckle 8 and/or the sensor target move in synchronization with the respiration of the occupant 11.

The detection unit 24 detects the received waves (i.e., reflected waves) to convert the changes made to high-frequency radio waves (i.e., transmitted waves) into changes in low frequencies.

Examples of the detection by the detection unit 24 include amplitude detection, frequency detection, and phase detection. The phase detection compares the phase of travelling waves of the output unit 23 with the phase of received waves inclusive of reflected waves, thereby producing a detection output which includes low frequency signals resulting from converting the I component having the same phase as the travelling waves and the Q component having a 90-degree phase difference relative to the travelling waves. The detection output is an example of the sensor output signal whose waveform changes in response to the movement of the object.

The amplitude of the detection output is calculated as $I^2+Q^2$. The effective power of the detection output is calculated by multiplying the voltage by the I component (i.e., in-phase component) of the current or by multiplying the current by the I component of the voltage. Calculating a tangent of the I component and the Q component provides a phase change of the reflected waves relative to the traveling waves. The detection output includes a cyclic vital-sign signal component representing a vital sign that is at least either respiration or pulse beat, and also includes a noncyclic shift signal component representing the shifting movement (i.e., body movement) of the object.

Figure 10:
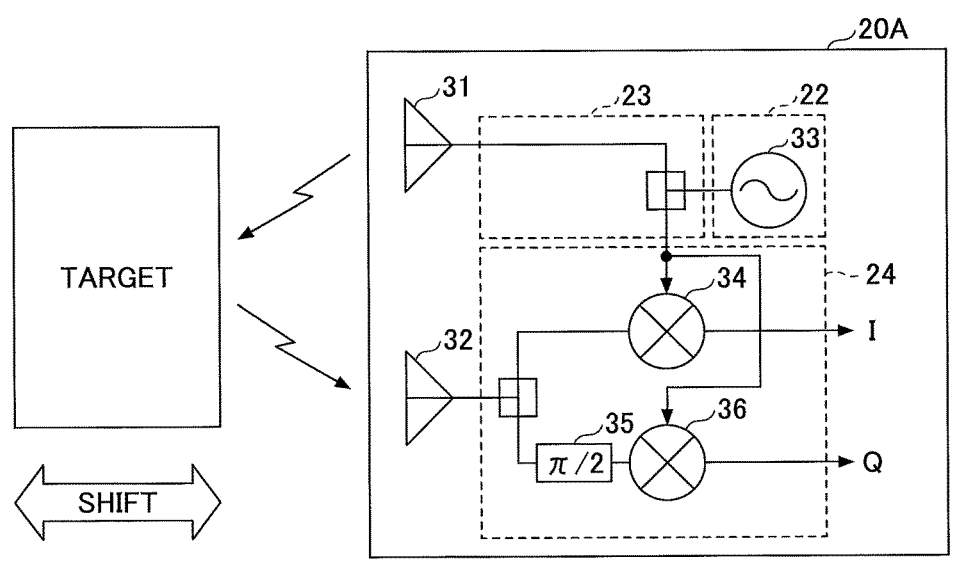
FIG. 10 is a drawing illustrating an example of the configuration of a Doppler sensor serving as an example of the sensor.

FIG. 10 is a drawing illustrating an example of the configuration of a Doppler sensor 20A serving as an example of the sensor 20.

The Doppler sensor 20A utilizes the Doppler effect to accurately detect a displacement of the sensor target based on the phase changes of reflected waves relative to the traveling waves. The movement of the sensor target causes the phase of reflected waves to change, which then causes the standing waves to change with a beat frequency responsive to the speed of this phase change. In consideration of this, the Doppler sensor 20A performs phase detection with respect to the transmitted waves and the reflected waves, thereby detecting a Doppler frequency proportional to the speed of a phase change of the reflected waves relative to the travelling waves. The use of the Doppler frequency allows the relative speed between the Doppler sensor 20A and the sensor target to be derived. Further, the Doppler sensor 20A may selectively detect Doppler frequencies, thereby discriminating between vehicle vibration, pulse beat, and respiration.

The frequency of vehicle vibration ranges from 5 Hz to 20 Hz. Examples of vehicle vibration include vibration caused by the travel of the vehicle, vibration caused by an impact on the vehicle, etc. A pulse beat frequency ranges from 1 Hz to 3 Hz. The frequency of respiration ranges from 0.5 Hz to 0.2 Hz. The faster the relative speed between the Doppler sensor 20A and the sensor target, the higher the Doppler frequency is. Vehicle vibration with large amplitude and high frequency is converted into a high Doppler frequency. Vehicle vibration can thus be easily removed by use of a filter, which allows selective extraction to be easily performed with respect to a shift signal component synchronized with the shifting movement (e.g., body movement) of the object and a vital-sign signal component synchronized with a vital sign that is at least either respiration or pulse beat.

The Doppler sensor 20A utilizes the Doppler effect to produce a Doppler frequency signal (i.e., an I output and a Q output) responsive to the frequency difference (i.e., Doppler frequency) between the transmitted waves and the received waves. The I output and the Q output are voltage signals having a phase difference of 90 degrees ($\pi/2$) with each other.

The Doppler sensor 20A includes an oscillator 33, a transmission antenna 31, a reception antenna 32, a delay circuit 35, and mixers 34 and 36. The oscillating signal of the oscillator 33 causes radio waves (e.g., microwaves) to be transmitted from the transmission antenna 31. Radio waves transmitted from the transmission antenna 31 are reflected by the sensor target on the seat 2. The reception antenna 32 receives the reflected waves. The delay circuit 35 imposes a 90-degree (i.e., $\pi/2$) phase delay on the received signal from the reception antenna 32. The mixer 34 receives the oscillating signal from the oscillator 33 and the received signal from the reception antenna 32 to produce an I output (i.e., I component). The mixer 36 receives the oscillating signal from the oscillator 33 and the received signal from the reception antenna 32 with the phase delay imposed by the delay circuit 35 to produce a Q output (i.e., Q component).

The transmission antenna 31 and the reception antenna 32 may be a planar patch antenna formed into a rectangular shape, for example. A plurality of transmission antennas 31 and a plurality of reception antennas 32 may be provided.

Figure 11A:
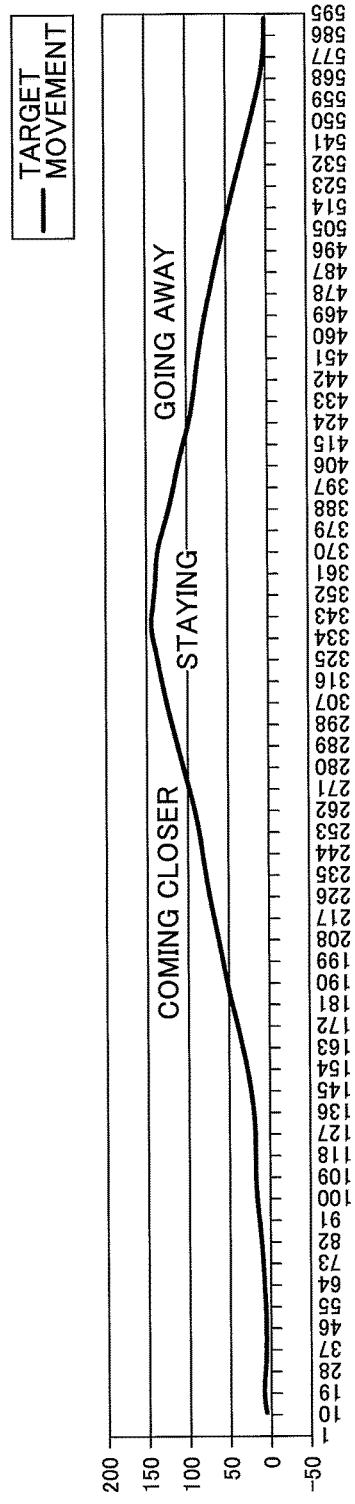
FIGS. 11A and 11B are drawings illustrating an example of the relationship between the movement of a sensor target and a detection output.
Figure 11B:
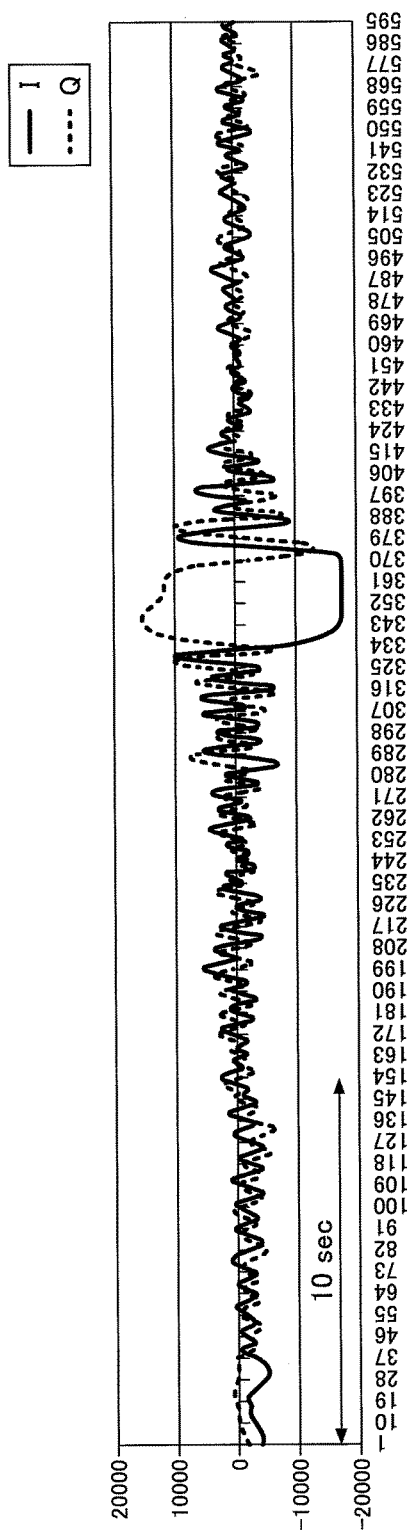

FIGS. 11A and 11B are drawings illustrating an example of the relationship between the shifting movement of a sensor target and a detection output. FIG. 11A illustrates the shifting movement of a sensor target. The horizontal axis represents a sample sequence number, and the vertical axis represents the phase change of reflected waves relative to traveling waves. FIG. 11B illustrates a detection output (i.e., I output and Q output). The horizontal axis represents a sample sequence number, and the vertical axis represents the amplitude of a detection output. The detection output can be used to detect a shift signal component synchronized with the shifting movement of the sensor target. For example, the detection unit 40 (see FIG. 3) may demodulate the I output and the Q output illustrated in FIG. 11B to calculate the phase change (i.e., rotation) of the reflected waves relative to the traveling waves, thereby detecting the shift signal component as illustrated in FIG. 11A.

Figure 12A:
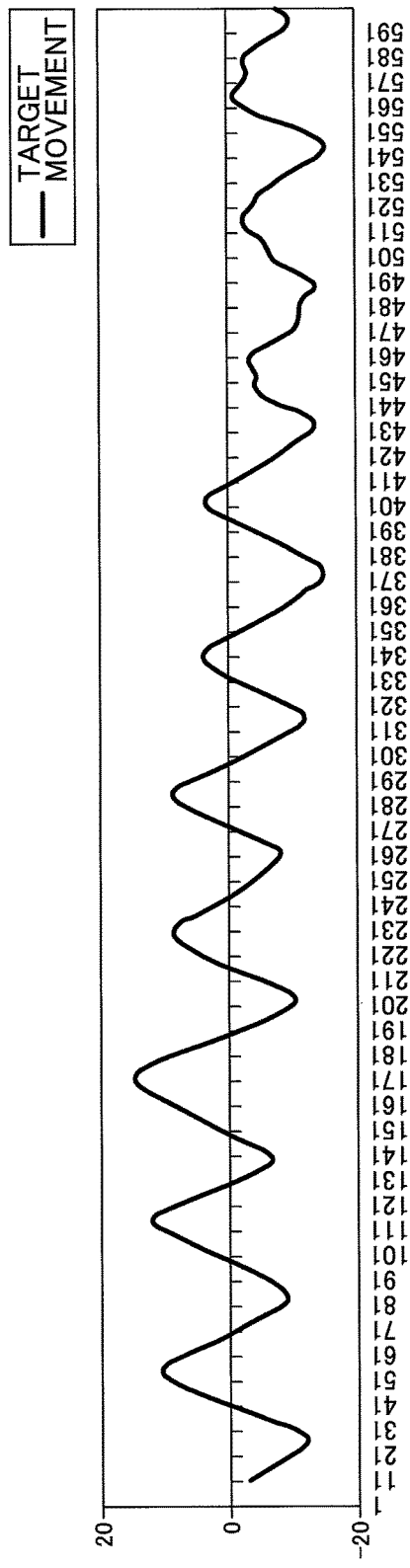
FIGS. 12A and 12B are drawings illustrating an example of the relationship between the displacement of a body surface of an occupant and a detection output.
Figure 12B:
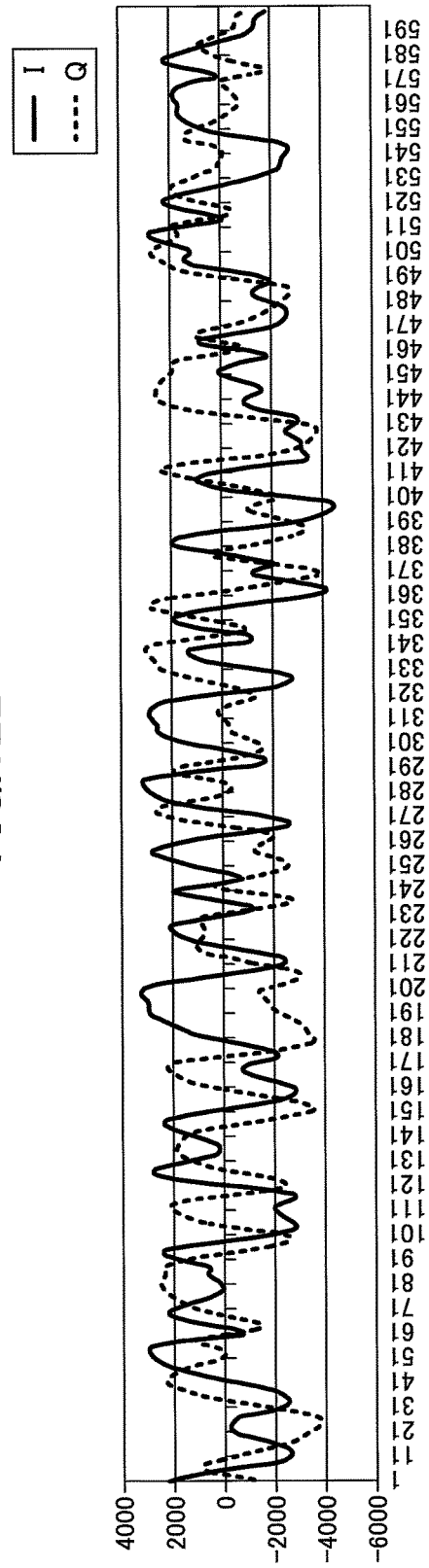

FIGS. 12A and 12B are drawings illustrating an example of the relationship between the displacement of a body surface of the occupant 11 and a detection output. FIG. 12A illustrates the displacement of a body surface of the occupant 11. FIG. 12B illustrates a detection output (i.e., I output and Q output). The horizontal axis represents a sample sequence number, and the vertical axis represents the amplitude of a detection output. The detection output can be used to detect the displacement of a body surface of the occupant 11. For example, the detection unit 40 (see FIG. 3) may demodulate the I output and the Q output illustrated in FIG. 12B to calculate the phase change (i.e., rotation) of the reflected waves relative to the traveling waves, thereby detecting the body surface displacement as illustrated in FIG. 12A.

Figure 13:
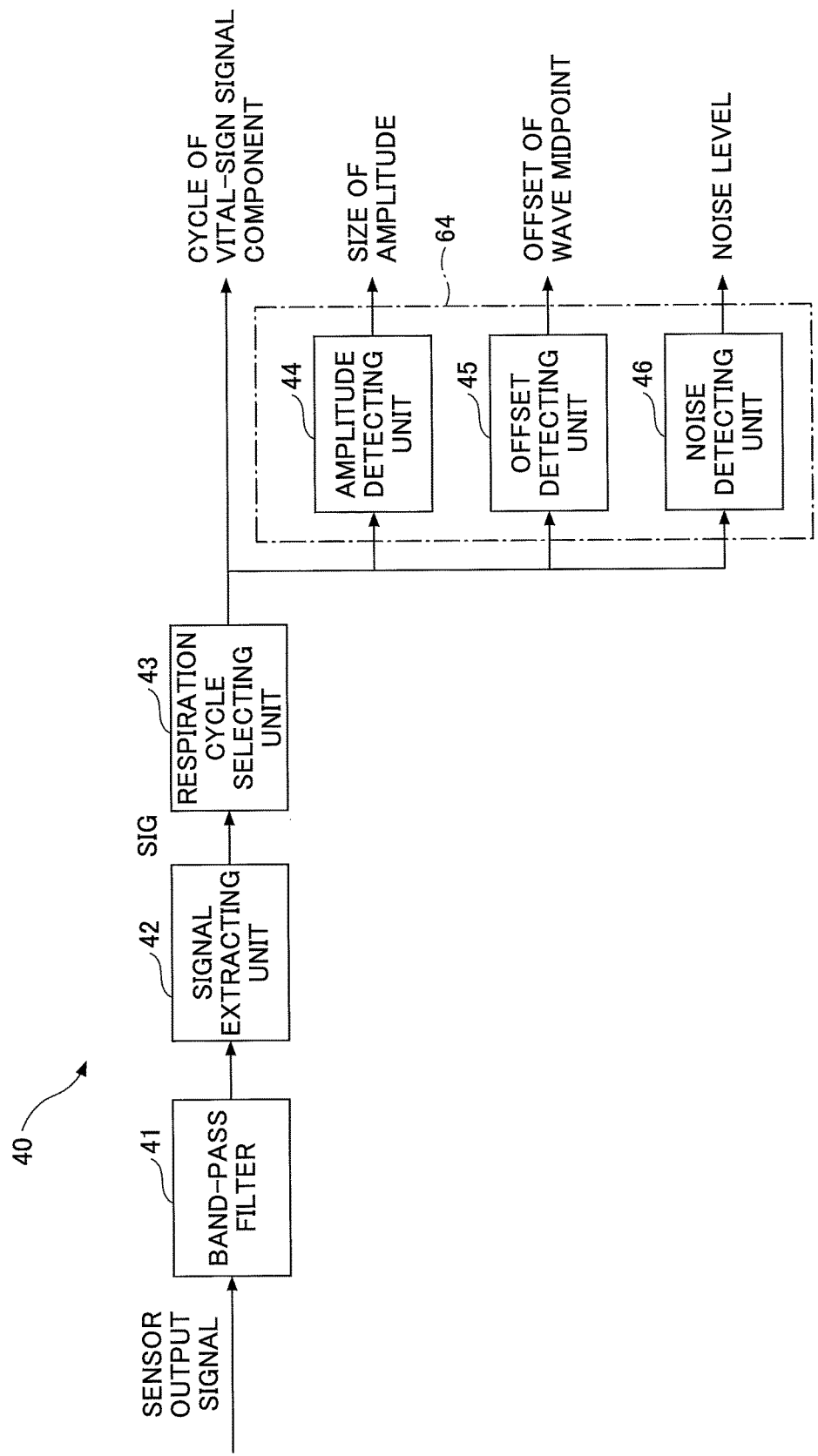
FIG. 13 is a drawing illustrating an example of the configuration of a detection unit.

FIG. 13 is a drawing illustrating an example of the configuration of the detection unit 40 (see FIG. 3). The detection unit 40 uses the detection output (i.e., an example of a sensor output signal) produced by the sensor 20 to detect a cycle of the vital-sign signal component indicative of a vital sign that is at least either respiration or pulse beat. The detection unit 40 receives a sensor output signal obtained by conversion into low frequencies through detection by the sensor 20. The detection unit 40 extracts significant features such as the movement of a sensor target from the received sensor output signal, and serves to selectively extracts the cyclic changes of a vital sign that is either respiration or pulse beat.

In the present embodiment, the detection unit 40 includes a band-pass filter 41, a signal extracting unit 42, a respiration cycle selecting unit 43, an amplitude detecting unit 44, and an offset detecting unit 45.

Figure 14:
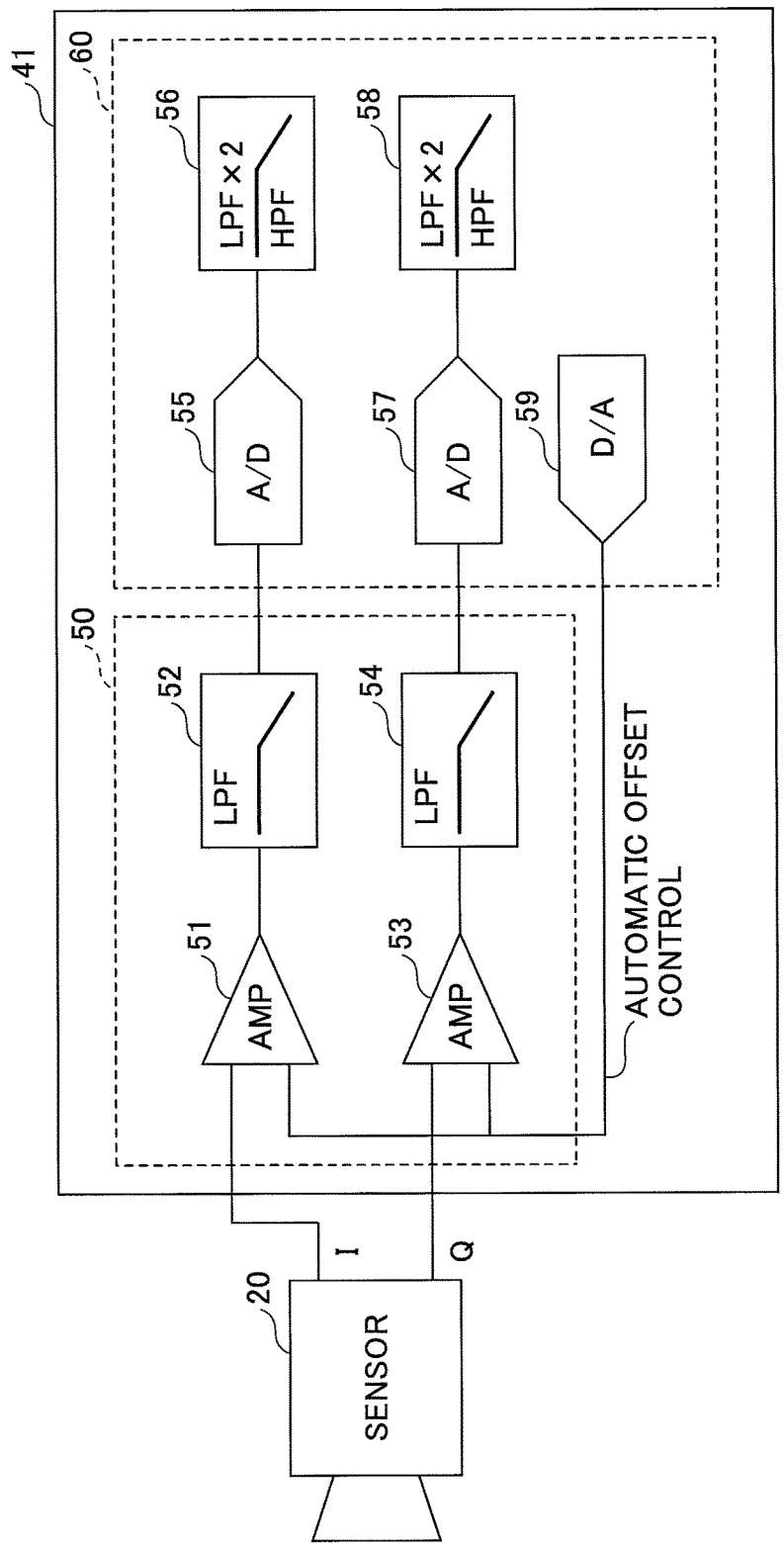
FIG. 14 is a drawing illustrating an example of the configuration of a band-pass filter.

FIG. 14 is a drawing illustrating an example of the configuration of the band-pass filter 41. The detection unit 40 serves as a preprocessing unit that performs preprocessing on the sensor output signal supplied from the sensor 20. The band-pass filter 41 allows signals lower than a predetermined frequency to pass therethrough. The band-pass filter 41 includes an analog circuit block 50 comprised of analog circuits and a digital circuit block 60 comprised of digital circuits.

The analog circuit block 50 determines the upper limit of passing frequencies based on the anti-alias frequency for A/D conversion. The band-pass filter 41 allows only the signals within a desired frequency band to pass therethrough to remove noise. The digital circuit block 60 performs A/D conversion with respect to the analog signals passing through the low-ass filters 52 and 54 of the analog circuit block 50, followed by performing digital processing for required band-pass signal processing.

A Doppler radar typically uses an alternating-current signal of 1 Hz or more for the purpose of detecting relative speed. The frequency (or cycle) of respiration ranges from 0.5 Hz to 0.2 Hz (or from 2 seconds to 5 seconds). The cycle of yawning is approximately 10 seconds, and the cycle of occupant shifting movement is approximately in a range of 20 seconds to 30 seconds. Attenuation spanning 30 seconds or longer by use of a capacitor-based CR filter may require the use of a large-volume capacitor. In such a case, stabilization at the time of power on takes a lengthy time. Further, it is not easy to have a large-volume capacitor embedded in the buckle because of space limitation.

In consideration of this, DC amplifiers 51 and 53 are used as analog amplifiers. The detection output produced by the sensor 20 includes a DC (direct-current) component. The analog circuit block 50 includes the DC amplifiers for amplifying the detection output produced by the sensor 20, and also includes low-pass filters for performing low-pass filtering with respect to the outputs of the DC amplifiers. The DC amplifier 51 amplifies the I output. The output of the DC amplifier 51 is applied to the low-pass filter 52. The DC amplifier 53 amplifies the Q output. The output of the DC amplifier 53 is applied to the low-pass filter 54.

The digital circuit block 60 includes an A/D conversion unit 55, a band-pass filter 56, an A/D conversion unit 57, a band-pass filter 58, and a D/A conversion unit 59. The A/D conversion unit 55 converts the analog output of the low-pass filter 52 into a digital output. The band-pass filter 56 allows the digital output of the A/D conversion unit 55 to pass through a predetermined frequency band. The A/D conversion unit 57 converts the analog output of the low-pass filter 54 into a digital output. The band-pass filter 58 allows the digital output of the A/D conversion unit 57 to pass through a predetermined frequency band. The D/A conversion unit 59 performs automatic digital control to adjust the offsets of the DC amplifiers 51 and 53 such that the DC amplifiers 51 and 53 are able to amplify signals without exceeding their ranges. The frequency (or cycle) of respiration ranges from 0.5 Hz to 0.2 Hz (or from 2 seconds to 5 seconds). A pulse beat frequency (or cycle) ranges from 3 Hz to 1 Hz (or from 0.5 seconds to 1 second). The frequency (or cycle) of occupant shifting movement ranges from 0.05 Hz to 0.03 Hz (or from 20 seconds to 30 seconds). Accordingly, high accuracy detection of respiration and occupant shifting movement (body shifting movement) require that the passband of the band-pass filter 41 is preferably set lower than or equal to 0.5 Hz that is the maximum frequency of respiration. Alternatively, high accuracy detection of pulse beat and occupant shifting movement (body shifting movement) require that the passband of the band-pass filter 41 is preferably set lower than or equal to 3 Hz that is the maximum pulse-beat frequency.

The signal extracting unit 42 (see FIG. 13) converts the output signal of the band-pass filter 41 limiting the frequency range of the detection output (which is an example of a sensor output signal) into a respiratory signal SIG (i.e., distance detection signal) proportional to the distance between the sensor target and the sensor 20.

The detection output of the sensor 20 includes an I output and a Q output, for example. The I output and the Q output are detected signals having a phase difference of 90 degrees with each other. A change in the distance between the sensor target and the sensor 20 causes the phase of reflected waves relative to transmitted waves to change. In the case of 24-GHz transmitted waves, a 6-mm change in the distance brings about a 360-degree phase change. A 30-mm change in the distance causes the phase to change by 1800 degrees (=360 degrees×30 mm/6 mm). A 1-mm change in the distance causes the phase to change by 60 degrees (=360 degrees×1 mm/6 mm). In this manner, phase rotation is equivalent to a change in the distance between the sensor target and the sensor 20.

In consideration of this, the signal extracting unit 42 calculates the angle of phase rotation from the detection output inclusive of the I output and the Q output, thereby deriving from the detection output the respiratory signal SIG indicative of the movement of the sensor target.

In the case of the phase rotation being smaller than 180 degrees, both the I output and the Q output contain information indicative of the amplitude of a signal that represents respiration. The signal extracting unit 42 is thus able to selectively use the I output and the Q output for the purpose of extracting the respiratory signal SIG when the amplitude is small. A signal source used for detection may selectively be used in response to the magnitude of the signal and the range of angular changes. Alternatively, a signal having increased reliability through weighting may be used. These arrangements serve to increase the accuracy of respiration detection.

Conversion performed by the signal extracting unit 42 refers to changes in physical parameters or changes in signal forms. The signal extracting unit 42 performs peak-hold detection, for example. Alternatively, the signal extracting unit 42 calculates phase rotation from the I output and the Q output, thereby changing physical parameters from the I output and the Q output into a signal proportional to the distance. Conversion performed by the signal extracting unit 42 also refers to a size change that makes this signal indicate a distance change in actual scale, or refers to a scale change that converts this signal into a signal in the log scale. In the range of phase rotation smaller than 90 degrees, the I output and the Q output can be converted directly into the distance scale.

The amplitude of a detection output is typically proportional to the square or cube of the distance between the sensor target and the sensor 20. In consideration of this, a lookup table or the like may be used to provide a correspondence between the signal and the distance in a nonlinear manner. Such a process may be incorporated into the conversion performed by the signal extracting unit 42. No action performed by the signal extracting unit 42 is also regarded as a conversion that multiplies the signal by a factor of "1".

The respiration cycle selecting unit 43 (see FIG. 13) uses the respiratory signal SIG (i.e., the distance detection signal proportional to the distance between the sensor target and the sensor 20) extracted by the signal extracting unit 42, thereby detecting therefrom the cycle of a vital-sign signal component inclusive of a respiratory cycle component.

The respiration cycle selecting unit 43 efficiently selects the cycle of a specific vital-sign signal component from the respiratory signal SIG. Further, the respiration cycle selecting unit 43 enhances the feature of a respiratory cycle component contained in the waveform of the respiratory signal SIG to produce a vital-sign signal component, followed by detecting peak points and/or zero-crossing points from the waveform of the produced vital-sign signal component to detect the respiration cycle. The respiration cycle is an example of the cycle of the vital-sign signal component.

Noise superimposed on the respiratory signal SIG adds error to the peak detection and the cycle detection. In consideration of this, the respiration cycle selecting unit 43 improves the waveform by enhancing the feature of a respiration cycle component contained in the waveform of the respiratory signal SIG, for example, thereby readily performing peak-to-peak detection and/or cycle detection.

In general, detection of a particular frequency component may be achieved by use of the FFT (fast Fourier transform).

The size of the amplitude of frequencies in a particular frequency range obtained by the FFT may be used to determine whether the frequency components indicative of respiration or pulse beat are present. It may be noted, however, that the cycle, offset, or waveform of a vital-sign signal component indicative of a vital sign that is at least either respiration or pulse beat changes form cycle to cycle. In the case of the FFT being used, thus, a signal waveform of each cycle may preferably be extracted and subjected to noise removal, followed by being processed by post-processing such as the FFT.

Biological signals relating to respiration or the like constantly change. Because of this, information indicative of a respiratory cycle contained in various signals output from the detection unit of the sensor 20 may be detected as a large magnitude signal in one component of the detection output, and may be detected as a small magnitude signal in another component of the detection output. Rather than relying on one signal, a plurality of vital-sign signals are selected from a plurality of signals, thereby improving the reliability of information regarding vital signs.

Figure 15:
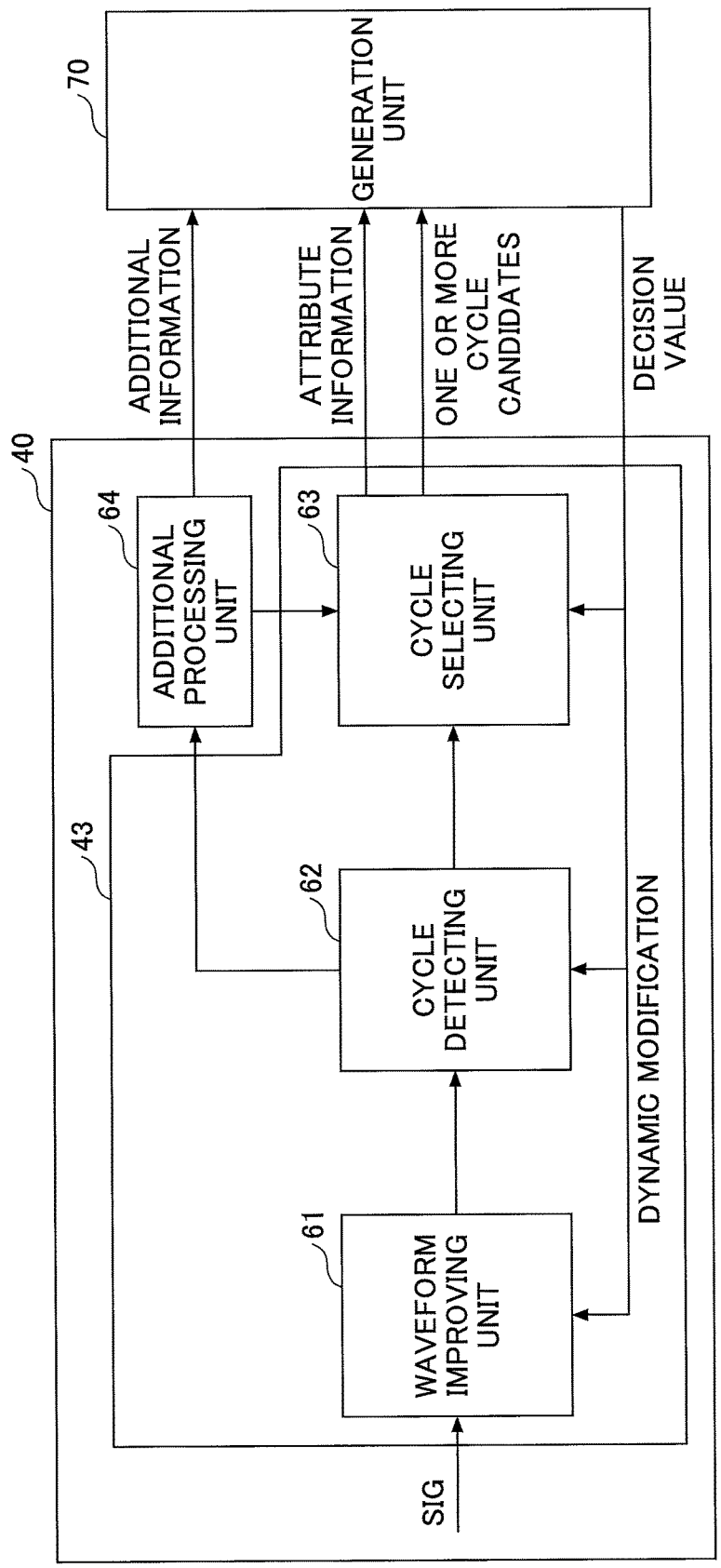
FIG. 15 is a drawing illustrating an example of the configuration of a respiration cycle selecting unit.

FIG. 15 is a drawing illustrating an example of the configuration of the respiration cycle selecting unit 43. The respiration cycle selecting unit 43 detects a plurality of cycles of respiration of the occupant 11 from a plurality of signals including the I output, the Q output, a phase signal, an amplitude signal, and the like, followed by selecting one or more of these cycles, and then transmitting the one or more selected cycles to the generation unit 70. The respiration cycle selecting unit 43 includes a waveform improving unit 61, a cycle detecting unit 62, and a cycle selecting unit 63.

In order to detect a respiration cycle, the waveform improving unit 61 performs arithmetic processes for enhancing the features (e.g., waveform peaks, zero-crossing points, inflection points, etc.) of respiration components contained in the waveform of the respiratory signal SIG. For example, the waveform improving unit 61 performs arithmetic processes such as filtering, obtaining differentials, multiplication, damping, and the like for the purpose of removing noise and offsets. The waveform improving unit 61 may perform a plurality of waveform improving processes with respect to a single respiratory signal SIG. A signal obtained through differentiation of the respiratory signal SIG includes information about a respiration cycle. The waveform improving unit 61 uses a plurality of waveform improving filters providing different waveform improving functions, respectively, to enhance the features of respiration cycle components contained in the waveform of the respiratory signal SIG, thereby generating a plurality of vital-sign signal components.

The cycle detecting unit 62 uses one or more detection units (i.e., cycle detection logic units) to detect the features of respiration cycle components contained in the one or more vital-sign signal components whose waveforms have been improved by the waveform improving unit 61, thereby detecting (i.e., deriving) one or more respiration cycles. The cycle detection logic units, which are an example of programs defining a method of detecting a cycle, may be implemented as a central processing unit. The cycle detecting unit 62 may use optimal detection units by taking into account differences between the features of respiration cycle components, thereby accurately detecting the features. Different features of waveform peaks may include a triangular peak, a trapezoid peak, a gentle curve peak, etc.

The cycle selecting unit 63 selects one or more candidate respiration cycles from the one or more respiration cycles detected by the cycle detecting unit 62. For example, the cycle selecting unit 63 selects, as a candidate respiration cycle, an average value or a middle value of the respiration cycles detected by the cycle detecting unit 62.

The cycle selecting unit 63 may select the average value or the middle value by taking into account weights given to the I output and the Q output in the case of the phase rotation being small (e.g., smaller than 90 degrees). The cycle selecting unit 63 may select the average value or the middle value by taking into account weights given to the phase signal or to the distance signal obtained from the I output and the Q output in the case of the phase rotation being large (e.g., 90 degrees or more). Weights may be given by taking into account not only the information about phase rotation but also amplitude size, fluctuation in signal cycles, etc.

In this manner, the respiration cycle selecting unit 43 of the detection unit 40 utilizes a plurality of cycle detection methods to detect the candidate cycles of vital-sign signal components from the sensor output signal produced by the sensor 20. This arrangement allows the generation unit 70 to identify a reliable cycle of a vital-sign signal component accurately from among the candidate cycles detected by the respiration cycle selecting unit 43.

The cycle selecting unit 63 sends the selected candidate respiration cycles together with attribute information of the selected candidate respiration cycles to the generation unit 70. The generation unit 70 utilizes the attribute information to evaluate the reliability of these selected candidate respiration cycles.

The number of candidate respiration cycles produced by the cycle selecting unit 63 may be two or more. For example, a middle value, the largest value, and the smallest value of the selected candidate respiration cycles may be sent to the generation unit 70.

In order to isolate the desired types of movement such as respiration and body shifting movement, the cycle selecting unit 63 may select at least one of the plurality of detection units (i.e., cycle detection logic units) to select the candidate respiration cycles, or may change at least one of the type and passband of the selecting filters for selecting the candidate respiration cycles. The cycle of a biological signal constantly changes. In consideration of this, the cycle selecting unit 63 may factor in the outcomes of reliability evaluation performed by the generation unit 70 or the vital-sign information generated from the candidate respiration cycles by the generation unit 70 to change at least one of the type of the selecting filters and the passband of the selecting filters. The cycle selecting unit 63 may utilize parallel computation of the selecting filters having different filter coefficients to select the candidate respiration cycles.

The respiration cycle selecting unit 43 performs one or more filtering processes and cycle detection processes with respect to one signal. The cycle of rapid respiration and the cycle of slow respiration may optimally be detected by different process parameters for detection processes. In consideration of this, the respiration cycle selecting unit 43 utilizes feedback information about vital signs generated by the generation unit 70 to change the methods of detecting the cycle of a vital-sign signal component, such that the reliability of the selected candidate cycles are improved for the generation unit 70. This arrangement allows a detection method suitable for a current respiration cycle to be selected.

There are cases in which a plurality of filtering processes and a plurality of cycle detection processes are unable to be performed in a parallel manner. In such cases, the respiration cycle selecting unit 43 takes into account the currently established respiration cycle fed back from the generation unit 70 to dynamically change the characteristics of filtering processes and the methods of detecting cycles, such that the amplitude and fluctuation of a target signal are reduced. This arrangement serves to improve the vital-sign information generated by the generation unit 70.

The detection unit 40 includes an additional processing unit 64 (see FIG. 15). As illustrated in FIG. 13, the additional processing unit 64 includes an amplitude detecting unit 44, an offset detecting unit 45, and a noise detecting unit 46.

The amplitude detecting unit 44 performs an additional process for detecting the amplitudes of the vital-sign signal components whose waveforms have been improved by the waveform improving unit 61, followed by sending the detected amplitudes to the generation unit 70 as additional information. The generation unit 70 reduces the reliability of the respiration cycles detected from the vital-sign signal components whose amplitudes, as detected by the amplitude detecting unit 44, are smaller than a predetermined amplitude.

The offset detecting unit 45 detects information about an offset with respect to the midpoint of the respiration wave and the like. By detecting offset information regarding the midpoint of the respiration wave and the like, the offset detecting unit 45 is able to detect a shift signal component indicative of the noncyclic shifting movement of the object.

The noise detecting unit 46 performs an additional process for detecting the noise levels of the vital-sign signal components whose waveforms have been improved by the waveform improving unit 61, followed by sending the detected noise levels to the generation unit 70 as additional information. A noise level is an indicator used in reliability evaluation of the candidate respiration cycles by the generation unit 70.

FIGS. 16A through 16E are drawings illustrating examples of signal waveforms processed by the detection unit 40. In FIGS. 16A through 16D, the detection unit 40 uses moving average filters for signal filtering.

In FIGS. 16A through 16D, the cycle selecting unit 63 uses, as a respiration cycle selecting filter, a moving average filter that produces a moving average over a period of ¼ to ½ of a reference respiration cycle. The offset detecting unit 45 (see FIG. 13) uses, as an offset detecting filter, a moving average filter that produces a moving average over a period equal to1to 2 times the reference respiration cycle. The amplitude detecting unit 44 (see FIG. 13) calculates a difference between the upper peak and lower peak of the wave of a vital-sign signal component. A moving average period may be variably set to a value suitable for an average respiration cycle evaluated as reliable by the generation unit 70, or may be selected based on the results of a plurality of moving average processes.

Figure 16A:
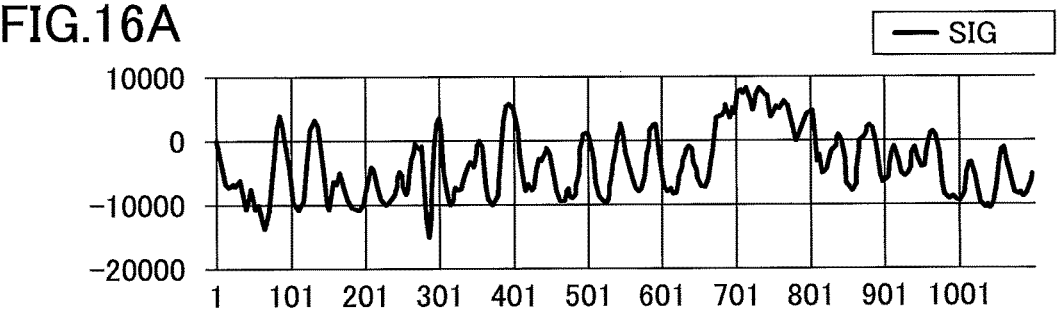
FIGS. 16A through 16E are drawings illustrating examples of signal waveforms processed by the detection unit.

FIG. 16A illustrates an example of the waveform of a respiratory signal SIG. The respiratory signal SIG extracted by the signal extracting unit 42 following the band-pass filter 41 includes components relating to vehicle vibration, body shifting movement, and respiration.

Figure 16B:
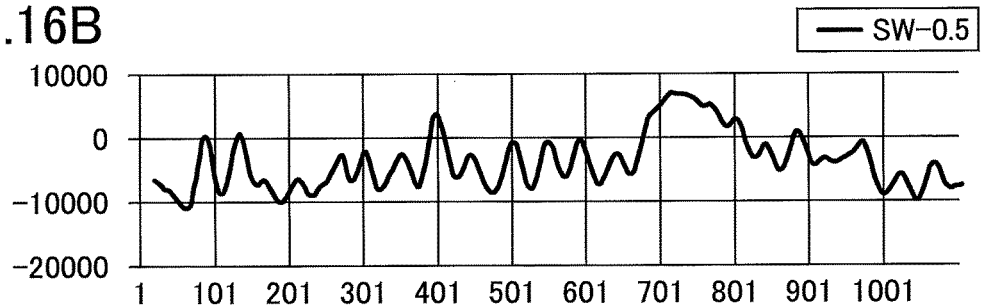

FIG. 16B illustrates an example of the waveform of a vital-sign signal component SW-0.5 that is generated by a moving average filter of the waveform improving unit 61 producing an moving average of the respiratory signal SIG over a period of ½ of the reference respiration cycle. A respiration cycle feature has become prominent through enhancement.

Figure 16C:
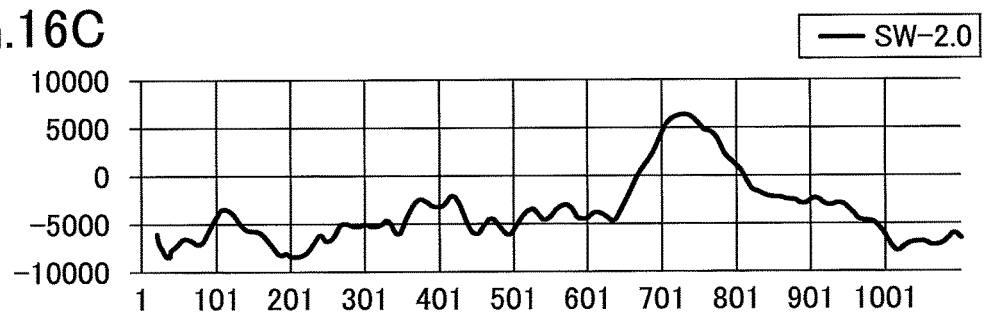

FIG. 16C illustrates an example of the waveform of a vital-sign signal component SW-2.0 that is generated by a moving average filter of the offset detecting unit 45 producing a moving average of the vital-sign signal component SW-0.5 over a period equal to 2 times the reference respiration cycle. The vital-sign signal component SW-2.0 represents the midpoint line of the wave while a respiration cycle feature is suppressed. Presence of a shift signal component indicative of the noncyclic shifting movement of the object causes changes in the vital-sign signal component SW-2.0.

Figure 16D:
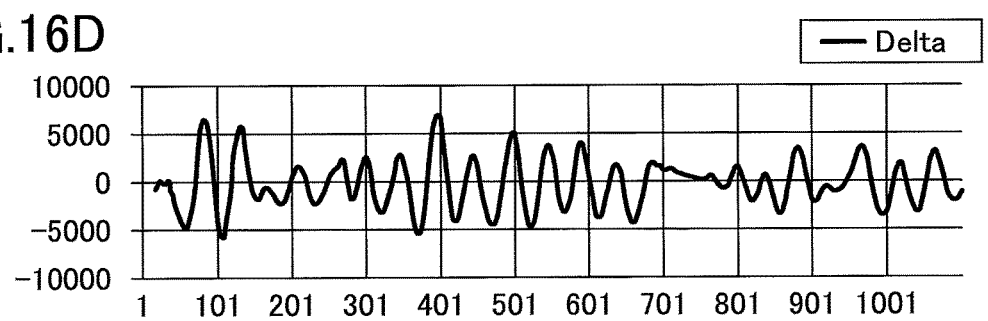

FIG. 16D illustrates an example of the waveform of a differential signal Delta that is generated by the waveform improving unit 61 deriving a differential between the vital-sign signal component SW-0.5 and the vital-sign signal component SW-2.0. The cycle detecting unit 62 detects a respiration cycle in the differential signal Delta. The cycle selecting unit 63 selects the respiration cycle detected in the differential signal Delta as a candidate respiration cycle.

Figure 16E:
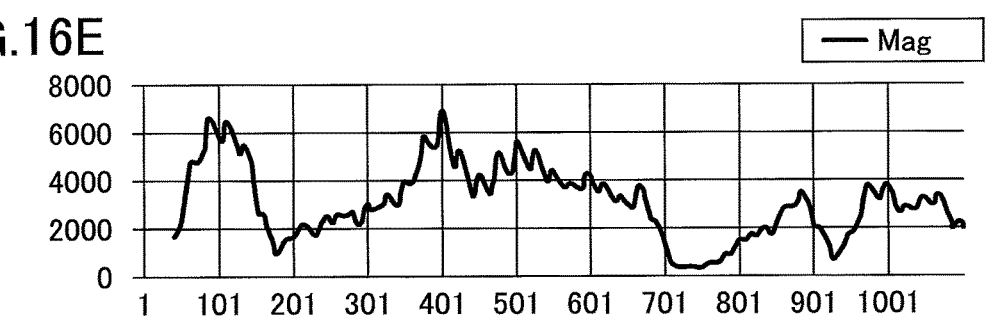

FIG. 16E illustrates an example of the waveform of an envelope Mag of the differential signal Delta detected by the amplitude detecting unit 44. The envelope Mag is an indicator used in reliability evaluation of the candidate respiration cycles by the generation unit 70.

Figure 17:
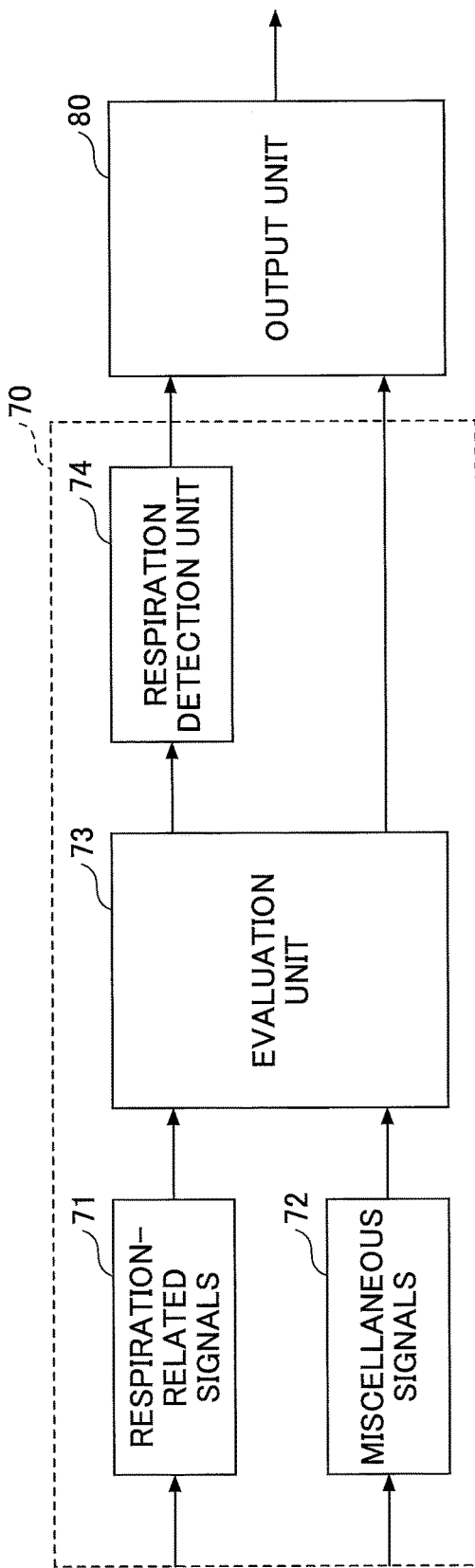
FIG. 17 is a drawing illustrating an example of the configuration of a generation unit.
Figure 18A:
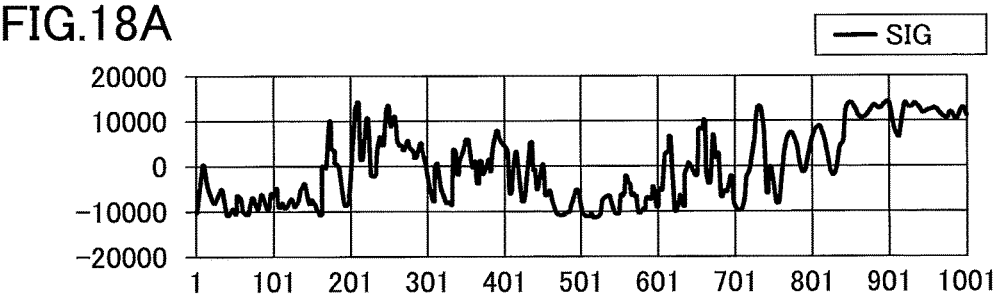
FIGS. 18A through 18E are drawings illustrating examples of signal waveforms processed by the detection unit.
Figure 18B:
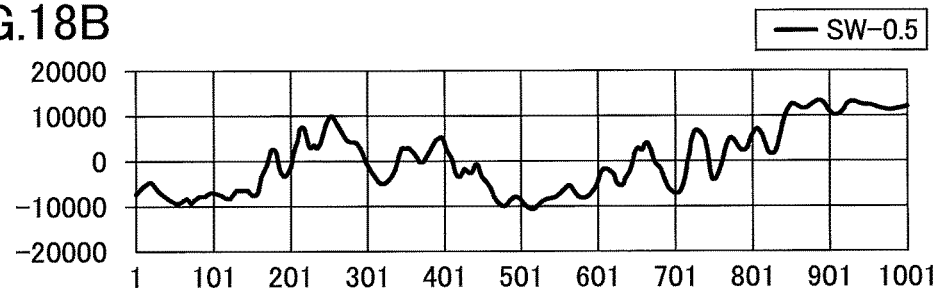
Figure 18C:
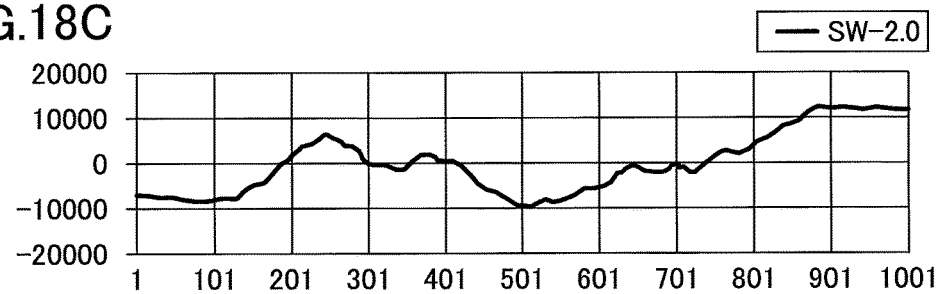
Figure 18D:
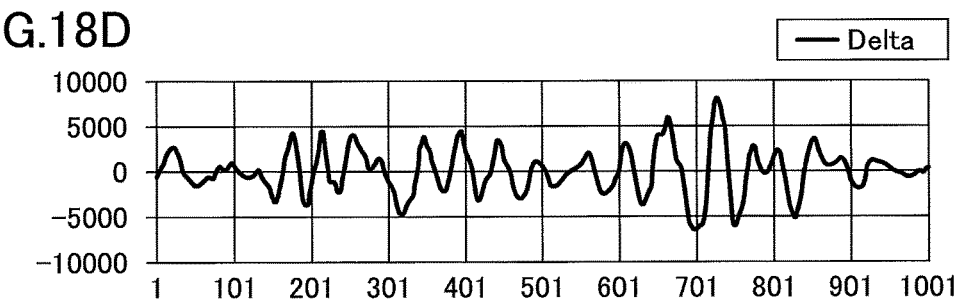
Figure 18E:
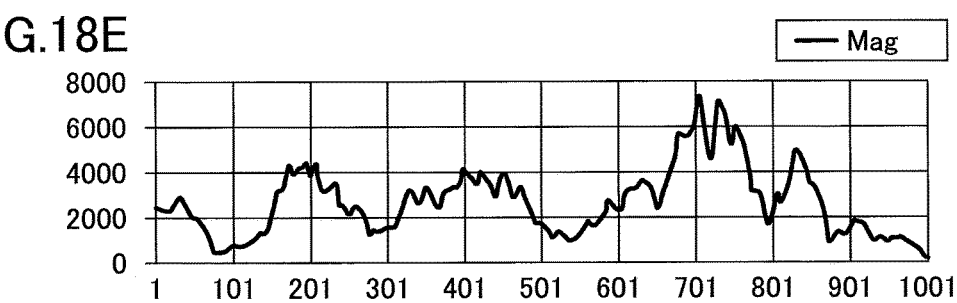

FIG. 17 is a drawing illustrating an example of the configuration of the generation unit 70. The generation unit 70 evaluates the reliability of vital-sign signal components detected by the detection unit 40 so as to generate, from a reliable vital-sign signal component, vital-sign information regarding a vital sign that is at least either respiration or pulse beat. In so doing, the generation unit 70 uses a reliable vital-sign signal component rather than less reliable vital-sign signal components to generate the vital-sign information.

In response to the signals (respiration-related signals 71 and miscellaneous signals 72) from the detection unit 40, the generation unit 70 determines the presence of respiration and the cycle of respiration by taking into account the reliability of candidate respiration cycles. The generation unit 70 includes an evaluation unit 73 for evaluating the reliability of candidate respiration cycles of vital-sign signal components detected by the detection unit 40, and also includes a respiration detection unit 74 for generating vital-sign information regarding a vital-sign. Vital-sign information includes a current status regarding the presence/absence of respiration, a current respiration cycle, an average respiration cycle, a voluntary respiration cycle, fluctuation in respiration, abnormal respiration, etc.

The evaluation unit 73 checks whether there is a shifting movement of the object on the seat 2. The evaluation unit 73 then gives higher reliability to a candidate respiration cycle detected in the absence of shifting movement than reliability given to a candidate respiration cycle detected in the presence of shifting movement. The shifting movement of the object on the seat 2 includes the movement of a driver's body made for the purpose of driving the vehicle, the movement of an object caused by the movement of the vehicle, etc. The respiration detection unit 74 uses a candidate respiration cycle of a vital-sign signal component that is more reliable than other candidate respiration cycles to generate vital-sign information. This arrangement serves to avoid generating vital-sign information from a less-reliable candidate respiration cycle of a vital-sign signal component.

The evaluation unit 73 checks whether there is an object on the seat 2 in response to the shift signal component detected by the offset detecting unit 45 of the detection unit 40. The evaluation unit 73 may check whether there is a shifting movement of the object on the seat 2 in response to vehicle behavior data indicative of the behavior of a vehicle that causes movement of the object on the seat 2. The evaluation unit 73 may combine the shift signal component and the vehicle behavior data to check whether there is a shifting movement of the object on the seat 2.

The evaluation unit 73 may give higher reliability to a candidate respiration cycle of a vital-sign signal component having a large amplitude detected by the amplitude detecting unit 44 of the detection unit 40 than reliability given to a candidate respiration cycle in the case of a small amplitude being detected by the amplitude detecting unit 44. The respiration detection unit 74 uses a candidate respiration cycle of a vital-sign signal component that is more reliable than other candidate respiration cycles to generate vital-sign information. This arrangement serves to avoid generating vital-sign information from a less-reliable candidate respiration cycle of a vital-sign signal component.

The evaluation unit 73 may give higher reliability to a candidate respiration cycle of a vital-sign signal component having a small noise level detected by the noise detecting unit 46 of the detection unit 40 than reliability given to a candidate respiration cycle in the case of a large noise level being detected by the noise detecting unit 46. The respiration detection unit 74 uses a candidate respiration cycle of a vital-sign signal component that is more reliable than other candidate respiration cycles to generate vital-sign information. This arrangement serves to avoid generating vital-sign information from a less-reliable candidate respiration cycle of a vital-sign signal component.

The evaluation unit 73 may give higher reliability to a candidate respiration cycle of a vital-sign signal component in the case of small variation being present in the candidate respiration cycles detected by the cycle selecting unit 63 of the detection unit 40 than reliability given to a candidate respiration cycle in the case of large variation being present in the candidate respiration cycles detected by the cycle selecting unit 63. The respiration detection unit 74 uses a vital-sign signal component that is more reliable than other vital-sign signal components to generate vital-sign information. This arrangement serves to avoid generating vital-sign information from a less-reliable candidate respiration cycle of a vital-sign signal component.

The respiration detection unit 74 may use a temporal change of the cycle of a vital-sign signal component that is more reliable than others to generate vital-sign information. This arrangement serves to improve the reliability of generated vital-sign information even when the cycle of a vital-sign signal component changes over time.

Specifically, the respiration detection unit 74 uses a temporal change of the cycle of a vital-sign signal component that is more reliable than others to select a period during which the cycle is stable, followed by generating vital-sign information from a segment of the vital-sign signal component in such a stable period. This arrangement ensures that a cycle of a vital-sign signal component as observed during a stable-cycle period is used to generate vital-sign information, thereby serving to improve the reliability of generated vital-sign information.

The respiration detection unit 74 may selectively collect voluntary respiration cycles during voluntary respiration to obtain their average, thereby identifying a voluntary respiration cycle. The respiration detection unit 74 may use the evaluation unit 73 to select a reliable respiration cycle, followed by outputting a current respiration cycle with its reliability. The respiration detection unit 74 may output an average respiration cycle that is an average of candidate respiration cycles in a section evaluated by the evaluation unit 73 as having a high reliability. The respiration detection unit 74 may output a respiration fluctuation that is the fluctuation of respiration observed in a section evaluated by the evaluation unit 73 as having a high reliability.

The evaluation unit 73 evaluates the reliability of candidate respiration cycles by using at least one of the evaluation criteria listed below:
(1) finding high reliability when a signal continues to have a cycle falling within a certain range (i.e., cycle variation is small, or an average cycle is stable);
(s) finding high reliability when a signal amplitude is larger than or equal to a certain level;
(3) finding high reliability when a body exhibits no large movement (i.e., no rapid change either in the offset or in the signal);
(4) finding high reliability when processing by the signal preprocessing unit and the signal extraction unit as well as a signal magnitude are proper (e.g., no occurrence of exceeding a range, no offset error, a passing signal having an amplitude falling within a proper range, etc.);
(5) finding high reliability when information other than respiration signals (e.g., vehicle travel data that is an example of the miscellaneous signals 72) indicates values within a particular range;
(6) with a plurality of candidate respiration cycles being given, finding high reliability for a candidate respiration cycle closest to the average or for a candidate respiration cycle selected by majority voting.

(7) finding high reliability for a cycle obtained by weighting, according to priority-based selection, or as a weighted average;
(8) finding high reliability when a seatbelt is on;
(9) finding high reliability when input information is believed to be reliable based on the current information for evaluation.

In accordance with the results of evaluation by the evaluation unit 73, the respiration detection unit 74 determines the presence/absence of current respiration, a current respiration cycle, an average respiration cycle, fluctuation in respiration, etc., based on the reliability information and reliable sections, followed by outputting the results of determination.

Such determined presence/absence of respiration, respiration cycles, cycle fluctuation, amplitudes, and so on can selectively be used by the output unit 80. Further, these determined factors will be able to be used at a later stage to determine occupant states such as yawing and no respiration.

In response to the results of determination made by the generation unit 70, the output unit 80 transmits information such as vital-sign information to the outside according to need. The output unit 80 transmits to the output one or more information items listed below:

(1) vital-sign information about the occupant, i.e., the presence/absence of respiration, a respiration cycle rank, a respiration stability state (i.e., reliability), or the like;
(2) vital signs about the occupant, i.e., data indicative of a respiration cycle, a respiration amplitude, the shifting movement of the body, etc.;
(3) information different from the vital-sign information (self-diagnosis information), i.e., self-diagnosis results (i.e., an indication of a normal state or an indication of an abnormal state); and
(4) additional information different from the vital-sign information, i.e., information indicative of the presence/absence of an occupant, information about the tension of a belt estimated from a respiration amplitude, etc.

Figure 19A:
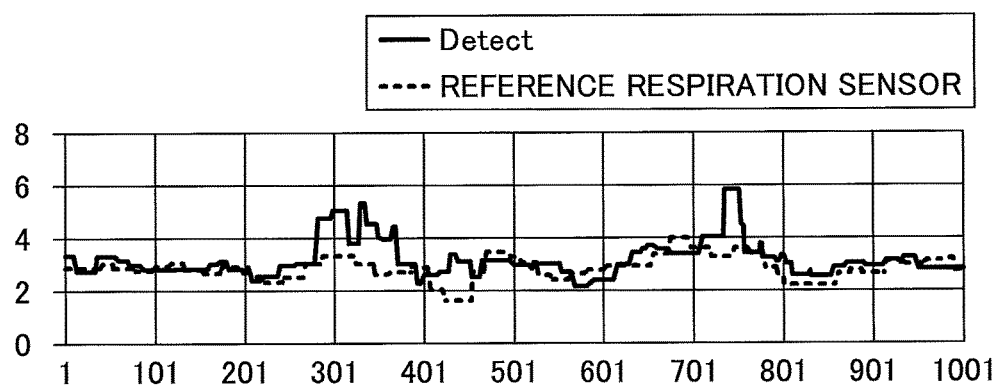
FIGS. 19A through 19C are drawings illustrating an example of deriving an occupant state based on the signal waveforms of FIGS. 18A through 18E.
Figure 19B:
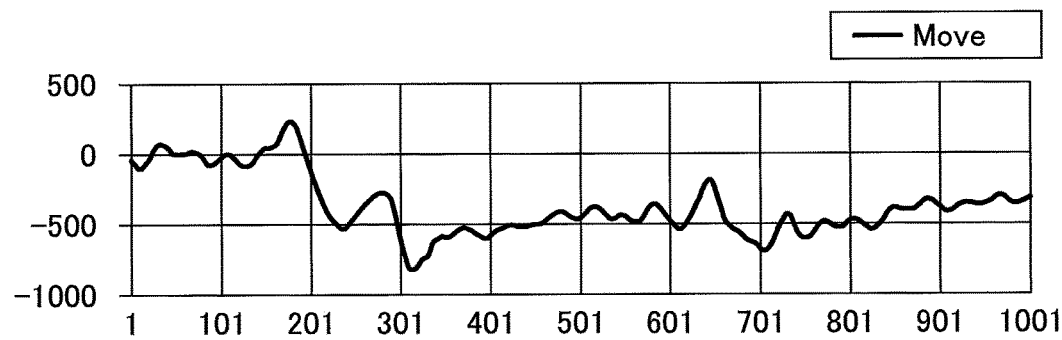
Figure 19C:
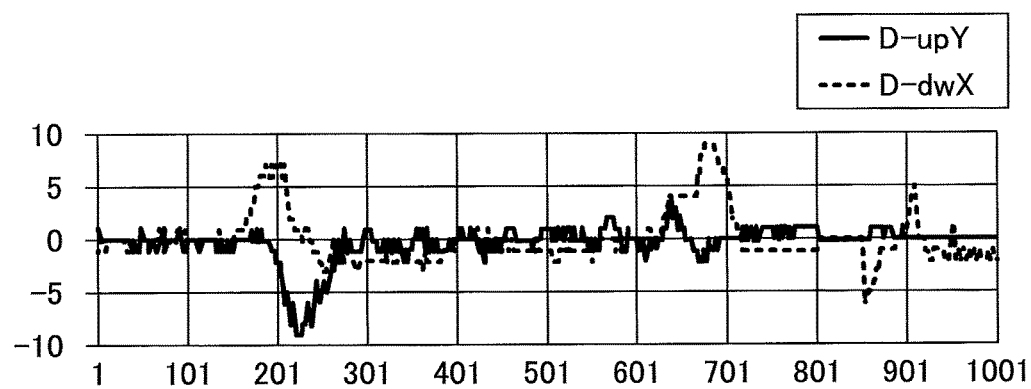

FIGS. 18A through 18E are drawings illustrating examples of signal waveforms processed by the detection unit 40. FIGS. 19A through 19C are drawings illustrating an example of deriving an occupant state based on the signal waveforms of FIGS. 18A through 18E. What FIGS. 18A through 18E represent are the same as FIGS. 16A through 16E, and a description thereof is omitted. In FIG. 19A, a waveform Detect illustrates temporal changes in the respiration cycle output (i.e., estimated) by the generation unit 70 (i.e., continuous changes in the respiration cycle over time). In FIG. 19A, a dashed line indicates temporal changes in the respiration actually detected by the respiration sensor. In FIG. 19B, a waveform Move indicates temporal changes in the shifting movement of the body (i.e., continuous changes in the shifting movement of the body over time). Sharp changes in the waveform Move correspond to the forward displacements of a chest caused by braking. In FIG. 19C, a waveform D-dwX illustrates a force applied to the occupant during deceleration of the vehicle, and a waveform D-upY illustrates a force applied to the occupant during the travel of the vehicle on a curve to the right.

In this example, a check as to whether the occupant is in a stable state is made as follows. The waveform Detect has sporadic, unstable periods in which the respiration cycle shows disturbance (i.e., a period from the 250-th sample point to the 370-th sample point as well as a period from the 700-th sample point to the 760-th sample point). In consideration of the data of the waveform Move, however, it is reasonably estimated that the disturbances in the respiration exhibited by the waveform Detect are attributable to disturbed detections caused by the shifting movement of the occupant. Namely, the respiration detection unit 74 can determine that the disturbances appearing in the respiration cycle during the same periods as the periods of sharp changes in the waveform Move are attributable to disturbances caused by the sudden movement of the body.

In the case of the vehicle behavior data illustrated in FIG. 19C being available, the respiration detection unit 74 may determine that such sudden movement of the body is attributable to passive movement of the body caused by a turn that is made after braking.

In this manner, external factors are removed from the information to focus on spontaneous body movements made during respiration periods only, which allows an occupant status to be derived that indicates that the spontaneous respiration cycle of the occupant is extremely stable.

Similarly, occupant reactions and body movements may be detected when a deviation from a stable state or no respiration is detected and when a warning in the form of sound, light, or a belt movement is given to the occupant from the vehicle, thereby checking an occupant status.

FIG. 20 is a block diagram illustrating the configuration of a seatbelt apparatus 1B serving as an example of an on-vehicle system. Using frequency in the VHF-UHF range as the oscillating frequency of the sensor 20 allows part of the propagating waves to reach some depth below the skin surface and to be reflected thereby. A change in the amount of blood flow thus causes a slight change in the amount of reflection. In the case of such a frequency being used, a change in the standing wave ratio is detected in consideration of a long wavelength thereof. Such a change includes a signal component responsive to a change in the distance between the sensor and the hip, a change in the area size of a reflective surface, a change in the reflectance caused by blood flow. Pulse beat ranges from 1 Hz to 3 Hz, and respiration ranges from 0.5 Hz to 0.2 Hz. Despite a difference in frequency between the target signals, the same method as in the detection of respiration may be used.

FIG. 20 illustrates the functional block configuration of a mechanism for detecting respiration and pulse beat. In this example, the sensor 20 is shared for the detection of respiration and for the detection of pulse beat while the detection unit 40 and the generation unit 70 have respective units dedicated for respiration and dedicated for pulse beat (i.e., a respiration detection unit 40A, a pulse beat detection unit 40B, generation units 70A and 70B).

Although the buckle and the on-vehicle system have been described by referring to the embodiments, the present invention is not limited to these embodiments. Various modifications and improvements such as combining or replacing an embodiment partially or entirely with one or more other embodiments may be made without departing from the scope of the present invention.

For example, the seat 2 may be a front seat in the vehicle, or may be a rear seat in the vehicle.

The present application is based on and claims the benefit of priority of Japanese priority application No. 2016-081279 filed on Apr. 14, 2016, with the Japanese Patent Office, the entire contents of which are hereby incorporated by reference.

What is claimed is:
1. A buckle, comprising:
a main body connectable to a tongue attached to a seatbelt of a vehicle;
a sensor disposed in the main body or in a support member that supports the main body, the sensor con- figured to produce a sensor output signal whose waveform changes in response to movement of an object situated in a seat of the vehicle or in response to a change of tension of the seatbelt;

a detection unit configured to extract, from the sensor output signal produced by the sensor, a detection signal indicative of the movement of an object, and to detect, from the detection signal, vital-sign signal components indicative of a vital sign that is at least either respiration or pulse beat;

a generation unit configured to evaluate reliability of the vital-sign signal components detected by the detection unit and to generate vital-sign information about the vital sign from a reliable one of the vital-sign signal components; and an output unit configured to output the vital-sign information generated by the generation unit;

wherein the detection unit is configured to obtain a first vital-sign component that indicates a moving average of the detection signal over a first period of time, to obtain a second vital-sign component that indicates a moving average of the detection signal over a second period of time differing in length from the first period of time, and to calculate a difference between the first vital-sign component and the second vital-sign component, and wherein the generation unit is configured to evaluate the reliability based on the difference.

2. The buckle as claimed in claim 1, wherein the generation unit is configured to determine whether there is a shifting movement of the object, to give higher reliability as the evaluated reliability in a case of absence of the shifting movement than in a case of presence of the shifting movement, and to generate the vital-sign information from the reliable one of the vital-sign signal components, the reliable one having higher reliability than a less reliable one of the vital-sign signal components.

3. The buckle as claimed in claim 2, wherein the detection unit is configured to detect, from the sensor output signal, a shift signal component indicative of the shifting movement of the object, and the generation unit is configured to determine whether the shifting movement of the object is present in response to the shift signal component detected by the detection unit.

4. The buckle as claimed in claim 2, wherein the generation unit is configured to determine whether the shifting movement of the object is present in response to vehicle behavior data indicative of behavior of the vehicle, the behavior of the vehicle causing the shifting movement of the object.

5. The buckle as claimed in claim 1, wherein the detection unit is configured to detect amplitudes of the vital-sign signal components, and the generation unit is configured to give higher reliability as the evaluated reliability in a case of a first amplitude being detected by the detection unit than in a case of a second amplitude being detected by the detection unit, the first amplitude being larger than the second amplitude, and to generate the vital-sign information from the reliable one of the vital-sign signal components, the reliable one having higher reliability than a less reliable one of the vital-sign signal components.

6. The buckle as claimed in claim 1, wherein the detection unit is configured to detect noise levels of the vital-sign signal components, and the generation unit is configured to give higher reliability as the evaluated reliability in a case of a first noise level being detected by the detection unit than in a case of a second noise level being detected by the detection unit, the first noise level being smaller than the second noise level, and to generate the vital-sign information from the reliable one of the vital-sign signal components, the reliable one having higher reliability than a less reliable one of the vital-sign signal components.

7. The buckle as claimed in claim 1, wherein the detection unit is configured to detect cycles of the vital-sign signal components, and the generation unit is configured to give higher reliability as the evaluated reliability in a case of a first cycle fluctuation being detected by the detection unit than in a case of a second cycle fluctuation being detected by the detection unit, the first cycle fluctuation being smaller than the second cycle fluctuation, and to generate the vital-sign information from the reliable one of the vital-sign signal components, the reliable one having higher reliability than a less reliable one of the vital-sign signal components.

8. The buckle as claimed in claim 1, wherein the detection unit is configured to detect cycles of the vital-sign signal components from the sensor output signal, and the generation unit is configured to generate the vital-sign information from a reliable cycle of the vital-sign signal components.

9. The buckle as claimed in claim 8, wherein the detection unit is configured to change methods of detecting the cycles of the vital-sign signal components in response to the vital-sign information that is generated and fed back by the generation unit, such that the reliability evaluated by the generation unit increases.

10. The buckle as claimed in claim 8, wherein the detection unit is configured to use a plurality of different cycle detecting methods to detect a plurality of cycle candidates for the vital-sign signal components from the sensor output signal, and the generation unit is configured to select from the plurality of cycle candidates the reliable cycle of the vital-sign signal components.

11. The buckle as claimed in claim 1, wherein the generation unit is configured to generate the vital-sign information based on temporal changes in a cycle of the reliable one of the vital-sign signal components.

12. The buckle as claimed in claim 11, wherein the generation unit is configured to select, based on the temporal changes, a stable time period in which the cycle is stable, and to generate the vital-sign information from the reliable one of the vital-sign signal components in the stable time period.

13. An on-vehicle system, comprising:

a buckle connectable to a tongue attached to a seatbelt of a vehicle;

a sensor disposed in the buckle or in a support member that supports the buckle, the sensor configured to produce a sensor output signal whose waveform changes in response to movement of an object situated in a seat of the vehicle;

a detection unit configured to extract, from the sensor output signal produced by the sensor, a detection signal indicative of the movement of an object, and to detect, front the detection signal, vital-sign signal components indicative of a vital sign that is at least either respiration or pulse beat;

a generation unit configured to evaluate reliability of the vital-sign signal components detected by the detection unit and to generate vital-sign information about the vital sign from a reliable one of the vital-sign signal components; and an output unit configured to output the vital-sign information generated by the generation unit;

wherein the detection unit is configured to obtain a first vital-sign component that indicates a moving average of the detection signal over a first period of time, to obtain a second vital-sign component that indicates a moving average of the detection signal over a second period of time differing in length from the first period of time, and to calculate a difference between the first vital-sign component and the second vital-sign component, and wherein the generation unit is configured to evaluate the reliability based on the difference.

14. An on-vehicle system, comprising:

a buckle connectable to a tongue attached to a seatbelt of a vehicle;

a sensor disposed in the buckle or in a support member that supports the buckle, the sensor configured to produce a sensor output signal whose waveform changes in response to a change of tension of the seatbelt;

a detection unit configured to extract, from the sensor output signal produced by the sensor, a detection signal indicative of the movement of an object, and to detect, from the detection signal, vital-sign signal components indicative of a vital sign that is at least either respiration or pulse beat;

a generation unit configured to evaluate reliability of the vital-sign signal components detected by the detection unit and to generate vital-sign information about the vital sign from a reliable one of the vital-sign signal components; and an output unit configured to output the vital-sign information generated by the generation unit;

wherein the detection unit is configured to obtain a first vital-sign component that indicates a moving average of the detection signal over a first period of time, to obtain a second vital-sign component that indicates a moving average of the detection signal over a second period of time differing in length from the first period of time, and to calculate a difference between the first vital-sign component and the second vital-sign component, and wherein the generation unit is configured to evaluate the reliability based on the difference.

* * * * *